United States Patent [19]

Huston et al.

[11] Patent Number: 5,482,858
[45] Date of Patent: * Jan. 9, 1996

[54] POLYPEPTIDE LINKERS FOR PRODUCTION OF BIOSYNTHETIC PROTEINS

[75] Inventors: James S. Huston, Chestnut Hill; Hermann Oppermann, Medway, both of Mass.

[73] Assignee: Creative BioMolecules, Inc., Hopkinton, Mass.

[*] Notice: The portion of the term of this patent subsequent to Feb. 25, 2009, has been disclaimed.

[21] Appl. No.: 139,171

[22] Filed: Oct. 19, 1993

Related U.S. Application Data

[63] Continuation of Ser. No. 955,399, Oct. 1, 1992, Pat. No. 5,258,498, which is a continuation of Ser. No. 342,449, Jan. 23, 1989, abandoned, which is a continuation-in-part of Ser. No. 52,800, May 21, 1987, abandoned.

[51] Int. Cl.$^6$ ............................... C12N 1/21; C12N 5/10; C12N 15/09
[52] U.S. Cl. .................... 435/252.33; 435/69.1; 435/69.7; 435/172.3; 435/240.2; 435/252.3; 435/320.1
[58] Field of Search ............................... 424/85.8, 85.91, 424/135.1, 136.1, 183.1; 435/69.1, 69.6, 69.7, 70.21, 172.2, 172.3, 240.27, 252.3, 252.33, 320.1; 530/387.3; 536/23.53

[56] References Cited

U.S. PATENT DOCUMENTS

| | | | |
|---|---|---|---|
| 4,355,023 | 10/1982 | Ehrlich et al. | 424/85.8 |
| 4,474,893 | 10/1984 | Reading | 436/547 |
| 4,642,334 | 2/1987 | Moore et al. | 530/388 |
| 4,666,837 | 5/1987 | Harford et al. | 435/68 |
| 4,704,692 | 11/1987 | Ladner | 364/496 |
| 4,946,778 | 8/1990 | Ladner et al. | 435/69.6 |
| 5,091,513 | 2/1992 | Huston et al. | 530/387.3 |
| 5,132,405 | 7/1992 | Huston et al. | 530/387.3 |
| 5,258,498 | 11/1993 | Huston et al. | 530/350 |
| 5,260,203 | 11/1993 | Ladner et al. | 435/172.3 |

FOREIGN PATENT DOCUMENTS

| | | |
|---|---|---|
| 0088994 | 9/1983 | European Pat. Off. . |
| 0120694 | 10/1984 | European Pat. Off. . |
| 0125023 | 11/1984 | European Pat. Off. . |
| 0171496 | 2/1986 | European Pat. Off. . |
| 0173494 | 3/1986 | European Pat. Off. . |
| 0184187 | 6/1986 | European Pat. Off. . |
| 0183964 | 6/1986 | European Pat. Off. . |
| 0193161 | 9/1986 | European Pat. Off. . |
| 0205326 | 12/1986 | European Pat. Off. . |
| 0239400 | 9/1987 | European Pat. Off. . |
| 2137631 | 10/1984 | United Kingdom . |
| 2188638A | 10/1987 | United Kingdom . |
| WO86/00090 | 1/1986 | WIPO . |
| WO87/02671 | 5/1987 | WIPO . |
| WO88/01649 | 3/1988 | WIPO . |
| WO88/01775 | 3/1988 | WIPO . |

OTHER PUBLICATIONS

Kabat et al. (1979) "Sequence of Immunoglobulin Chains," NIH Publication No. 80–2008 pp. 1–107.
Klausner, A. (1986) "'Single–Chain' Antibodies Become a Reality," *Biotechnology* 4:1041–1043.
Nishimura et al. (1987) "Recombinant Human–Mouse Chimeric Monoclonal Antibody Specific for Common Acute Lymphocytic Leukemia Antigen," *Cancer Research* 47:999–1005.
Tonegawa et al. (1977) "Cloning of an Immunoglobulin Variable Region Gene from Mouse Embryo," *Proc. Natl. Acad. Sci. USA* 74:3518–3522.
Verhoeyen et al. (1988) "Reshaping Human Antibodies: Grafting an Antilysozyme Activity," *Science* 239:1534–1536.
[00f4]Dammacao et al., "An Unusual Papain Fragment Containing the $V_H$ Region Of An IgG3 Myelmoa Protein," (Sep. 3, 1972) *J. Immunol.* 109:565–569.
Inbar, et al., "Localization of Antibody–Combining Sites Within The Variable Portions of Heavy and Light Chains," (Sep., 1972) *Proc. Natl. Acad. Sci. USA* 69:2659–2662.
Huston, et al., "Properties of the FD Fragment From Rabbit Immunoglobin G," (1972) *Biochemistry* 11:4256–4262.
Hochman, et al., "An Active Fragment (Fv) Composed of the Variable Portions of Heavy and Light Chains," (1973) *Biochemistry* 12:1130–1135.
Sharon, et al., "Preparation of Fv Fragment From The Mouse Myeloma XRPC–25 Immunoglobin Possessing Anti–Dinitrophenyl Activity," (1976) *Biochemistry* 15:1591–1594.
Itakura, et al., "Expression in *Escherichia coli* of a Chemically Synthesized Gene For The Hormone Somatostatin," (1977) *Science* 198:1056–1063.
Kabat, et al.,"Variable Region Genes For The Immunoglobin Framework Are Assembled From Small Segments of DNA—A Hypothesis," (May, 1978) *Proc. Natl. Acad. Sci USA* 75:2429–2433.

(List continued on next page.)

*Primary Examiner*—Robert D. Budens
*Attorney, Agent, or Firm*—Testa, Hurwitz & Thibeault

[57] ABSTRACT

Disclosed are a family of synthetic proteins having binding affinity for a preselected antigen, and multifunctional proteins having such affinity. The proteins are characterized by one or more sequences of amino acids constituting a region which behaves as a biosynthetic antibody binding site (BABS). The sites comprise $V_H$-$V_L$ or $V_L$-$V_H$-like single chains wherein the $V_H$ and $V_L$-like sequences are attached by a polypeptide linker, or individual $V_H$ or $V_L$-like domains. The binding domains comprise linked CDR and FR regions, which may be derived from separate immunoglobulins. The proteins may also include other polypeptide sequences which function, e.g., as an enzyme, toxin, binding site, or site for attachment to an immobilization media or radioactive atom. Methods are disclosed for producing the proteins, for designing BABS having any specificity that can be elicited by in vivo generation of antibody, for producing analogs thereof, and for producing multifunctional synthetic proteins which are self-targeted by virtue of their binding site region.

7 Claims, 50 Drawing Sheets

OTHER PUBLICATIONS

Rosenblatt, et al., "Isolation of an Active Variable–Domain Fragment From A Homogenous Rabbit Antibody Heavy Chain," (1978) *Biochemistry* 17:3877–3882.

Ehrlich, et al., "Isolation of an Active Heavy–Chain Variable Domain From A Homogenous Rabbit Antibody by Cathespin B Digestion of the Aminoethylated Heavy Chain," (1980) *Biochemistry* 19:4091–4096.

Wetzel, et al., "Expression in *Escherichia coli* of a Chemically Synthesized Gene For A Mini-C Analog of Human Proinsulin," (1981) *Gene* 16:63–71.

Rice, et al., "Regulated Expression of an Immunoglobulin k Gene Introduced Into a Mouse Lymphoid Cell Line," (Dec., 1982) *Proc. Natl. Acad. Sci. USA* 79:7862–7865.

Haber, Edgar, "Antibodies As Models For Rational Drug Design," (1983) *Biochem. Pharmacol.* 32:1967–1977.

Cabilly, et al., "Generation of Antibody Activity From Immunoglobulin Polypeptide Chains Produced in *Escherichia coli*," (Jun., 1984) *Proc. Natl. Acad. Sci. USA* 81:3273–3277.

Boulianne, et al., "Production of Functional Chimaeric Mouse/Human Antibody," (Dec., 1984) *Nature* 312:643–646.

Neuberger, et al., "Recombinant Antibodies Possessing Novel Effector Functions," (Dec., 1984) *Nature* 312:604–608.

Takeda, et al., "Construction of Chimaeric Processed Immunoglobulin Genes Containing Mouse Variable and Human Constant Region Sequences," (Apr., 1985) *Nature* 314:452–454.

Ohno, et al., "Antigen–Binding Specificities of Antibodies Are Primarily Determined by Seven Residues of $V_H$," (May, 1985) *Proc. Natl. Acad. Sci. USA* 82:2945–2949.

Marx, Jean L., "Antibodies Made to Order," (Aug., 1985) *Science* 229:455–456.

Morrison, Sherie L., "Transfectomas Provide Novel Chimeric Antibodies," (Sep., 1985) *Science* 229:1202–1207.

Tan, et al., "A Human–Mouse Chimeric Immunoglobulin Gene With A Human Variable Region Is Expressed In Mouse Myeloma Cells," (Nov., 1985) *Journ. of Immun.* 135:3564–3567.

Baer, et al., "Fusion of an Immunoglobulin Variable Gene And A T Cell Receptor Constant Gene In The Chromosome 14 Inversion Associated With T Cell Tumors," (1985) *Cell* 43:705–713.

Haber, et al., "The Antibody Combining Site," (1985) *Hybridoma Techn. In The Biosciences and Medicine.*

Huston, James S., "Engineering of Antibody Binding Sites To Tumor Antigens," (Jan. 27, 1986) Abstract B.

Williams, et al., "Production of Antibody–Tagged Enzymes By Myeloma Cells: Application to DNA Polymerase I Klenow Fragment," (1986) *Gene* 43:319–324.

Jones, et al., "Replacing The Complementarity–Determining Regions In A Human Antibody With Those From A Mouse," (May, 1986) *Nature* 321:522–525.

Van Brunt, Jennifer, "Protein Architecture: Designing From The Ground Up," (Apr., 1986) *BioTechnology* 4:277–283.

Sahagan, et al., "A Genetically Engineered Murin/Human Chimeric Antibody Retains Specificity For Human Tumor–Associated Antigen," (1986) *Journ. of Immun.* 137:1066–1074.

Arnon, Ruth, "Immunotargeted Chemotherapy In Cancer Research," Aug. 4, 1986) *Chemical Abstracts* vol. 105, No. 5.

Neuberger, M. S., "Novel Antibodies by DNA Transfection," (1986) *Mammalian Pathol. Biochem.* 105:95611.

"Genex Makes a Miniaturized Monoclonal Antibody," (Oct. 20, 1986) *Newswatch* 5.

Tramontano, et al., "Catalytic Antibodies," (Oct., 1986) *Science* 234:1566–1570.

Greenberg, Susan, "Genex Designs Single–Chain Antibodies, Patents Sought," (1986).

Pollack, et al., "Selective Chemical Catalysis by an Antibody," (1986) Science 234:1570–1573.

Sun, et al., "Chimeric Antibodies With 17–1A–Derived Variable And Human Constant Regions," (1986) *Hybridoma* 5:S17–S20.

Liu, et al., "Expression of Mouse: Human Immunoglobulin Heavy–Chain cDNA in Lymphoid Cells," (1987) *Elsevier Sci. Publ. BV* 33–40.

Sun, et al., "Chimeric Antibody With Human Constant Regions And Mouse Variable Regions Directed Against Carcinoma–Associated Antigen 17–1A," (Jan., 1987) *Proc. Natl. Acad. Sci. USA* 84:214–218.

Thiesen, et al., "Selective Killing of Human Bladder Cancer Cells by Combined Treatment With A and B Chain Ricin Antibody Conjugates," (1987) *Pharmacology* 106:37.

Corvalen, et al., "Construction and Characterization of a Hybrid–Hybrid Monoclonal Antibody Recognising Both Carcinoembryonic Antigen (CEA) And Vinca Alkaloids," (1987) *Cancer Immunol. Immunother* 24:127–132.

Chotia, et al., "Canonical Structures For The Hypervariable Regions of Immunoglobulins," (1987) *J. Mol. Biol.* 196:901–917.

Gascoigne, et al., "Secretion of a Chimeric T–Cell Receptor Immunoglobulin Protein," (May, 1987) *Proc. Natl. Acad. Sci. USA* 84:2936–2940.

Liu, et al., "Chimeric Mouse–Human IgG1 Antibody Than Can Mediate Lysis Of Cancer Cells," (May, 1987) *Proc. Natl. Acad. Sci. USA* 84:3429–3443.

Brown, et al., "Tumor–Specific Genetically Engineered Murine/Human Chimeric Monoclonal Antibody," (1987) *Cancer Res.* 47:3577–3583.

Richardson, et al., "The Radiolabeling of Antibodies For Use In Tumor Location and Treatment," (1987) *Chemical Abstracts* 107:330.

Boulianne, et al., "Biological Properties of Chimeric Antibodies," (1987) *Mol. Biol. Med.* 4:37–49.

Vogel, Carl–Wilhelm, "Current Approaches of Immunotargeting," (1987) Oxford University Press, pp. 3–7.

Schultz, P. G., "The Interplay Between Chemistry and Biology In The Design of Enzymatic Catalysts," (Apr., 1988) *Science* 240:426–432.

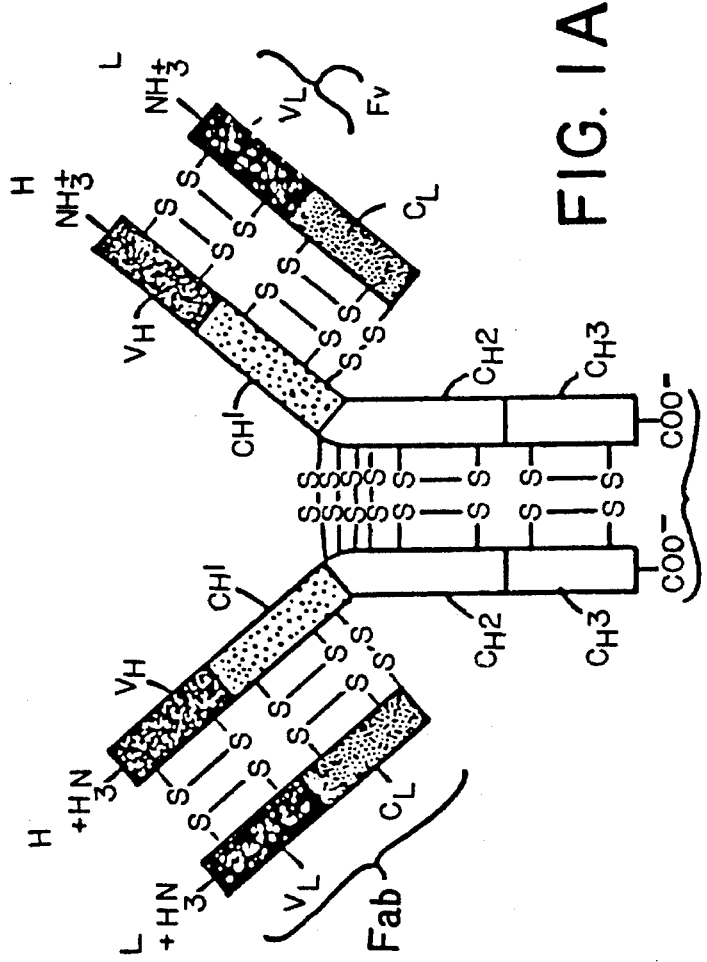

g-loop:
QVQLQQSGPELVEPGASVRISCTASGYTFTNYYIHWLKQRPGQGLEWIGWIYPGNGNTK

YNENFKGKATLTADKSSSTAFNQISSLTSEDSAVYFCARYTHYYF DYWGQGTTLTVSSK*

26-10:
EVQLQQSGPELVKPGASVRMSCKSSGYIFTDFYMNWVRQSHGKSLDYIGYISPYSGVTG

YNQKFKGKATLTVDKSSSTAYMELRSLTSEDSAVYYCAGSSGNKWAMDYWGHGASVTVSS*

26-10/g-loop hybrid:
EVQLQQSGPELVKPGASVRMSCKSSGYtftnyyihwlkQSHGKSLewigwiypgngntkynenfkgK
                          (cdr1-------)     (cdr2----------------)
                  hphI          bstXI   xbaI                    draI ATLTaDKSSSTAYMELRSLTSECSAVYYCArythyyf DYWGHGASVTVSS*
- - }                        (cdr3-----)
 hincII         sacII                 nheI newm/g-loop hybrid:
EVQLQQSGPGLVRPSQTLSLTCTVSGStftnyyihwlkQPPGRGLewigwiypgngntkynenfkg
        ---------           ----------------------
     [newm1...........]           [newm2..]
       avaII..........hphI     bstXI...xbaI
                                                narI
    RVTMLVDTSKNQFSLRLSSVTAADTAVYYCArythyyf DVWGQGSLVTVSS*
                                  ---------
     [newm3....................]              [newm4]
      draI.....................sacII       ...........

newm:
EVQLQQSGPGLVRPSQTLSLTCTVSGSTFSNDYYTWVRQPPGRGLEWIGYVFYHGTSDDTTP

LRS RVTMLVDTSKNQFSLRLSSVTAADTAVYYCARNLIAGCIDVWGQGSLVTVSS*

```
         10        20        30        40        50        60        70
GAATTCGAAGTTCAACTGCAACTGCCAGCAGTCCTGAATTGGTTAAACCTGCCCCTCTGTCTCGCCATGTCCT
GluPheGluValGlnLeuGlnSerGlyProGluLeuValLysProGlyAlaSerValArgMetSerC
AsuII           BbvI  AvaII                        AhaII        HhaI
EcoRI           Fnu4HI Sau96I                       BanI        HinPI
 TaqI            PstI                                EcoRII      HstNlaIII
                                                     HaeII       FspI
                                                     HhaI
                                                     HinPI
                                                     NarI
                                                     NlaIV
                                                     ScrFI
                                                     AcyI 80        90       100       110       120       130       140
GCAAATCCTCTGGGTACATTTCACCGACTTCTACATTTCGGTTCGCCAGTCTCCATGGTAAGTCTCT
ysLysSerGlyTyrIlePheThrAspPheTyrMetAsnTrpValArgGlnSerHisGlyLysSerLe
        RsaI     HphI                       NlaIII      BstXI NlaIII     Xba
                                                                         Ma 150       160       170       180       190       200       210
AGACTACATCGGGTACATTTCCCATACTCTCGGGTTACCCGGTTACAACCAGAAGTTTAAAGGTAAGGCCG
uAspTyrIleGlyTyrIleSerProTyrSerGlyValThrGlyTyrAsnGlnLysPheLysGlyLysAla
 RsaI                                        BstEII            DraI
                                              HpaII
                                              MaeIII
eI
```

```
        220          230          240          250          260          270          280
ACCCTTACTGTCGACAAATCTTCCTTCAACTGCTTACATGGAGCTGCCGTTCTTTGACCTCTGAGGACTCCG
ThrLeuThrValAspLysSerSerThrAlaTyrMetGluLeuArgSerLeuThrSerGluAspSerA
         AccI     MboII                  AluI                     DdeI HinfIFn   Sac
         HincII                           NlaIIIBbvI                              
         SalI                                  Fnu4HI
         TaqI 290          300          310          320          330          340          350
CGGTATACTATTGCGCGGCCTCTCTGGTAACAAATGGGCCATGGATTACTGGGTCATGGGCGCCTCTGT
laValTyrTyrCysAlaGlySerSerGlyAsnLysTrpAlaMetAspTyrTrpGlyHisGlyAlaSerVa
uDII   HhaIBanII       HaeIII     HaeIII           AhaII         Ma
IIAccI     FnuDII                 NcoI             BanI
           HinPINlaIV              NlaIII          HaeII
                                   Sau96I          HhaI
                                   StyI            HinPI
                                                   NarI
                                                   NlaIII
                                                   NlaIV
                                                   AcyI 360          370
TACTGTATCCTCCTCATAGGATCC
lThrValSerSer*amAsp
eIII       BamHI
           NlaIV
           Sau3A
           XhoII
```

```
          10         20         30.        40         50         60         70
GAATTCGACCTCCTAATGACCCAGACTCCGCTCTCTGCCCGTTTCTCTGGGTGACCAGGCTTCTATTT
GluPheAspValValMetThrGlnThrProLeuSerLeuProValSerLeuGlyAspGlnAlaSerIleS
EcoRI AatII                  HinfI          RpaII       BstEII
      AhaII                                             HphI EcoRII
      TaqI                                                   ScrFI
      AcyI                                              MaeIII
      MaeII 80         90         100        110        120        130        140
CTTGCCCTCTTCCCAGTCTCTGGTCTCCATTCTAATGGTAACACTTACCTGAACTGGTACCTGCAAAAGGC
erCysArgSerSerGlnSerLeuValHisSerAsnGlyAsnThrTyrLeuAsnTrpTyrLeuGlnLysAl
   Fnu4HI          AvaII       MaeIII     Hg1EII       BanI
   MboII           BstXI                               KpnI
                   Sau96I                              NlaIV
                                                       RsaI
```

```
         150          160          170          180          190          200          210
TGGTCAGTCTCCCGAAGCTTCTGATCTCTACAAGTTCTACAACCGTCTAACCGTCTGATCTCTGGTGTCCCGGATCCGTTCTCT
aGlyGlnSerProLysLeuLeuIleTyrLysValSerAsnArgPheSerGlyValProAspArgPheSer
            AluI Sau3A                                          HpaII
            HindIII                                              NciISau3A
                                                                 ScrFI 220          230          240          250          260          270          280
GGTTCTGGTTCTGGTACTGACTTCACCCTGAAGATCTCTCGTGTCCGAGGCCCAGGATCTCTGGTATCTACT
GlySerGlySerGlyThrAspPheThrLeuLysIleSerArgValGluAlaGluAspAspLeuGlyIleTyrP
Rsal      HphI     BglII              TaqIHaeIII Sau3A
                   MboII                         XhoII
                   Sau3A
                   XhoII 290          300          310          320          330          340          350
TCTCCTCTCAGACTACTCATGTACCCGCCACCTTCGGCGGTGCCACCAAGCTTCGAGATCAAACGTTGAGGATCC
heCysSerGlnThrThrHisValProProThrPheGlyGlyGlyThrLysLeuGluIleLysArg*op
DdeI        NlaIII  HgiEII        BanI   AluI  Sau3A MaeII   BamHI
            RsaI                  NlaIV        AvaI          NlaIV
                                               TaqI          Sau3A
                                               XhoI          XhoII
```

```
            10        20        30        40        50        60        70
GAATTCCAAGTTCAACTGCAGCCAGTCTCCTGAATTCCTTAAACCTGGTTAAACCTGCCCCCTCTGTCCTGCCCATGTCCT
GluPheGluValGlnLeuGlnSerGlyProGluLeuValLysProGlyAlaSerValArgMetSerC
AsuII    BbvI    AvaII                 AhaII     HhaI
EcoRI    Fnu4HI  Sau96I                 BanI      HinPI
         TaqI                 PstI      EcoRII    MstINlaIII
                                        HaeII     FspI
                                        HhaI
                                        HinPI
                                        NarI
                                        NlaIV
                                        AcyI 80        90        100       110       120       130       140
GCAAATCCTCTCGGTACATTTTCACCAATTACTACATCCATTGGTTCGCCAGTCTCTCATTGGTAAGTCTCT
ysLysSerSerGlyTyrIlePheThrAsnTyrTyrIleHisTrpValArgGlnSerHisGlyLysSerLe
                RsaI      HphI                            BstXI    NlaIII  Xba
            CATGTAAAAGTGGTTAATGATGTAGGTAACGCGGTC                           Ma
                            FokI 150       160       170       180       190       200       210
AGACTACATCGGGTCCGATCTCTACCCCGGGTAATCGGTAACACTAAGTACTACAATGAGAACTTTAAAGGTAAG
uAspTyrIleGlyProGlyAsnGlyAsnThrLysTyrTyrAsnGluAsnPheLysGlyLys
            TGATGTCTCCCACCTAGAGATGGGCCCATTACCATTGTGATTCATGATGTTACTCTTGAAA
            Sau3A AvaI   HpaII   MaeIIIDdeIRsaI                Drag
            XhoI        NciI            ScaI
                        NciI
                        SmaI
                        XmaI
```

```
        220         230         240         250         260         270         280
GCGACCCTTACTGTCTGACAAATCTTCCTCAACTGCCTTACATGGAGCTGCCTGCCTTCTTTGACCTCTGAGGACT
AlaThrLeuThrValAspLysSerSerThrAlaTyrMetGluLeuArgSerLeuThrSerGluAspSer
                  AccI      MboII                  AluI                    DdeI HinfI
                  HincII                            NlaIIIBbvI
                  SalI                                   Fnu4HI
                  TaqI 290         300         310         320         330         340         350
CCGCGGTATACTATTGCGGCGGCCTCCTCGGTAACAAATGGGCCCTTCGATTACTGGGGTCATGGCCGCC
erAlaValTyrTyrCysAlaGlySerSerGlyAsnLysTrpAlaPheAspTyrTrpGlyHisGlyAlaSe
                                              GGAAGCTAATGACCCCAGTACGC
  FnuDII   AccI    HhaIBanII  MaeIII     HaeIII                    AhaII
  SacII            FnuDII                 Sau96ITaqI                BanI
                   HinPINlaIV                                       HaeII
                                                                    HhaI
                                                                    HinPI
                                                                    NarI
        360         370                                             NlaIII
TGTTACTGTATCCCTCATAGGATCC                                           NlaIV
rValThrValSerSer*am                                                 AcyI
MaeIII      BamHI
            NlaIV
            Sau3A
            XhoII
```

```
         10        20        30        40        50        60        70
GAATTCGACGTCGTAATGACCCAGACTCCGCTGTCTCTGCCGTTTCTCTGCCTGACCAGGCTTCTATTT
GluPheAspValValMetThrGlnThrProLeuSerLeuProValSerLeuProAspGlnAlaSerIleS
EcoRI AatII                              HpaII   BstEII
      AhaII                                      HphI EcoRII
      TaqI                               HinfI         ScrFI
      AcyI                                             MaeIII
      MaeII 80        90       100       110       120       130       140
CTTGCCCTCTTCCCAGTCTATTGTGCCACTCTAATGGTAACACTTACCTGGATTGGTACCTGCAAAAGGC
AACGGGAGAAGGGTCAGATAACACGGTGAGATTACCATTGTGAATGGACCTAAC
erCysArgSerSerGlnSerIleValHisSerAsnGlyAsnThrTyrLeuAspTrpTyrLeuGlnLysAl
         Fnu4HI           HgiAI                  MaeIII    EcoRII  BanI
         MboII                                              ScrFI  KpnI
                                                            HgiEII NlaIV
                                                                   RsaI 150       160       170       180       190       200       210
TGGTCAGTCTCCGAAGCTTCTGATCTACAAAGTCTCTAACCGCTTCTCTGGTGTCCCGGATCGTTTCTCT
aGlyGlnSerProLysLeuLeuIleTyrLysValSerAsnArgPheSerGlyValProAspArgPheSer
         AluI   Sau3A                                      HpaII
                HindIII                                    NciISau3A
                                                                 ScrFI
```

```
          220         230         240         250         260         270         280
GGTTCTGGTTCTCTGGTACTGACTTCACCCTGAAGATCTCTCGTGTCGAGGCCCGAGGATCTCGGTATCTACT
                                                             CGCTCCTAGACCATAGATGA
GlySerGlySerGlyThrAspPheThrLeuLysIleSerArgValGluAlaGluAspLeuGlyIleTyrT
          RsaI     HphI         BglII        TaqIHaeIII Sau3A
                                MboII                   XhoII
                                Sau3A
                                XhoII 290         300         310         320         330         340         350
ACTCCTTCCAGGGGTCTCATGTACCGTGGCGGTTCGGCCCTTCGGCTGGCACCAAGCTTCGAGATCAAACCTTGAGGATCC
TGACGAAGGTCCCCAGAGTACATGGCACCGCCAAGCCGGGAAGCCGACCGTGGTTCGAGCT
yrCysPheGlnGlySerHisValProTrpThrPheGlyGlyGlyThrLysLeuGluIleLysArg*op
     EcoRII  NlaIII  RsaI    AvaII        BanI  AluI  Sau3A MaeII  BamHI
     ScrFI           RsaI    Sau96I       NlaIV       AvaI         NlaIV
                            HgiEII                   TaqI          Sau3A
                                                     XhoI          XhoII
```

```
         10        20        30        40        50        60        70
GAATTCATGGAAGTACAACTGCAACAATCTGGGCCCGGTCTCTGGTACCTCCTGTCTCAGACTCTGTCCCTGA
GluPheMetGluValGlnLeuGlnLeuGlnSerGlyProGlyLeuValArgProSerGlnThrLeuSerLeuT
EcoRINlaIII RsaI                  ApaIHpaII   RsaI     DdeIHinfI
                                  BanII       HaeII    Tth111I
                                  HaeIII
                                  NciI
                                  NlaIV
                                  Sau96I
                                  Sau96I
                                  ScrFI 80        90       100       110       120       130       140
CTTGTACCGTATCCGGATCCACCTTCTCTAACTACTACATCCATTGGGTCCGTCAACCGCCGGGTCGTCGG
hrCysThrValSerGlySerThrPheSerAsnTyrTyrIleHisTrpValArgGlnProProGlyArgGl
RsaI        BamHI              FokI           AvaIHincII HpaII
            HpaII                              NlaIV      NciI
            NlaIV                              Sau96I     ScrFI
            Sau3A
            XhoII 150       160       170       180       190       200       210
TCTCCAGTGGATCCGTTGGATTTACCCGGGTAATGGTAACACTAAGTACTACAATGAGAACTTTAAAGGC
yLeuGluTrpIleGlyTrpIleTyrProGlyTyrAsnGlyAsnThrLysTyrTyrAsnGluAsnPheLysGly
AvaI   Sau3A       AvaI       HaeIIIDdeIRsaI                    DraI    Sp
TaqI                Hpall                    ScaI
XhoI                NciI
                    NciI
                    ScrFI
                    ScrFI
                    SmaI
                    XmaI
```

```
        220       230       240       250       260       270       280
ATGCTGGTCGACACTTCTAAGAACCAATTCTCTCTGCGTCTGCTTCTGTTCTTGCGGCTGTCTTACCGCGGCGCTGATACTGCTG
MetLeuValAspThrSerLysAsnGlnPheSerLeuArgLeuSerSerValThrAlaAlaAspThrAlaV
laIII AccI      DdeIXmnI              Hgal  MboII HaeIIIFnu4HI
hI   HincII                                  BbvII     FnuDII
     SalI                                               SacII
      TaqI 290       300       310       320       330       340       350
TGTACTACTGCGCCGCCGTTCCTCCGGGTAATAAGTGGGACCATTTGATTACTGGGCCCAGGGCTCTCTGGTCAC
alTyrTyrCysAlaArgSerGlyAsnLysTrpAspHisLeuIleThrGlyProGlyGlnGlySerLeuValTh
RsaI BssHII     HpaII                       NlaIV BanII        BstEII HphI
         FnuDII                                    EcoRII              HaeIII
           FnuDII                                   HaeIII
           HhaI                                     Sau96I
           HinPI                                    ScrFI
           HinPI 360       370
CGTATCCTCTTAACTGCAG
rValSerSer*ocLeuGln
            PstI
```

```
              10        20        30        40        50        60        70
         GAATTCATGGAATCTGTCTGACTCAGCCGCCCGTCTGTATCTGGTGCCACCCGGTCAACGGGTAACTATCT
         GluPheMetGluSerValLeuThrGlnProProSerValSerGlyAlaProGlyGlnArgValThrIleS
         EcoRI  HinfI            DdeIFnu4HI                 HgiAIHpaII  FnuDII
             NlaIII              HinfI                        NciIHincII MaeIII
             XmnI                                               ScrFI   MluI 80        90       100       110       120       130       140
         CTTGCCGGTTCCTCTCCAGTCTTGTCCATTCTAATGGCCAACACTTATCTGGAATCTGAATGTACCAACACTGCC
         erCysArgSerSerGlnSerIleValHisSerAsnGlyAsnThrTyrLeuGluTrpTyrGlnGlnLeuPr
                DdeI      BstXI                                  BanI         Hp
                                                                 KpnI         Nc
                                                                 NlaIV        Sc
                                                                 RsaI 150       160       170       180       190       200       210
         GGGCACCCGCGGCCCGAAGCTGCTGATCTTTAAAGTATCTAATCGCTTCTCTGGCCGTACCGGATCGATTCTCT
         oGlyThrAlaProLysLeuLeuIlePheLysValSerAsnArgPheSerGlyArgThrGlyIleAspSerLeu
         aII FnuDII AluI   DraI                              RsaI ClaI
          II    HhaI   BbvI  Sau3A                                HpaII HinfI
          rFI  HinPI    Fnu4HI                                       Sau3A
          BanI                                                         TaqI
          NlaIV
```

```
         220          230          240          250          260          270          280
GTATCTAAGTCTCGGCCTCCTCTGCCACTCTGGCGATCACTGGTCTGCAAGCAGAAGATGAGCCCGATTACT
ValSerLysSerGlySerGlySerAlaThrLeuAlaIleThrGlyLeuGlnAlaGluAlaAspGluAspTyrT
  DdeI       NlaIV    BglI          Sau3A                       MboII   HaeIII 290          300          310          320          330          340          350
ACTGTTTTCAAGGCTCTCATGTACCGTGGACCGTACTACCTTCGGTGGCCACCAAGCTTACTGTACTGCGTCAGCC
yrCysPheGlnGlySerHisValProTrpThrPheGlyGlyGlyThrLysLeuThrValLeuArgGlnPr
           NlaIII    AvaII            BanI     AluI       RsaI HgaI
           RsaI      Sau96I            NlaIV   HindIII
                     HglEII 360
GTAACTGCAG
o*ocLeuGln
    PstI
MaeIII
```

```
         10        20        30        40        50        60        70
GAAGTTCAACTGCAGCAGTCTGGTCCTGAATTGGTTAAACCTGGCGCCTCTGTGCGCATGTCCTGCAAATCCTCT
 E  V  Q  L  Q  Q  S  G  P  E  L  V  K  P  G  A  S  V  R  M  S  C  K  S  S
         BbvI+     AvaII                  AhaII    HhaI                   MnlI+
         Fnu4HI    Sau96I                  BanI MnlI+ HinPI                FR-1
         PstI                                   EcoRII   FspIN1lIII
                                                HaeII    NspHI
                                                HhaI
                                                HinPI
                                                NarI
                                                NlaIV
                                                ScrFI

X₁|              FR-2            X₂|         125       135       145
    85        95        105       115            125       135       145
GGGTACCGGCCAGTCTTCATGGTAAGTCTCTAGACTTTAAGGGAAGCCGGAAATTTAAGGGTAAGGCCGACCCTTACTGTCGACAAATCTTCCTCA
 G  Y  R  Q  S  H  G  K  S  L  D  F  K  G  K  A  T  L  T  V  D  K  S  S  S
 BanI  BstXI  NlaIII        XbaI                          AcoI    MboII
 KpnI                                                     HincII  MnlI+
 NlaIV                                                    SalI
 RsaI                                            DraI     TaqI
```

FR-3
        160       170       180       190       200       210       220
ACTGCTTACATGGAGCTGCGTTCTTTGACCTCTGAGGACTCCGCGGTATACTATTGCGCGGTATCGATTATTGG
 T  A  Y  M  E  L  R  S  L  T  S  E  D  S  A  V  Y  Y  C  A  R  I  D  Y  W
                       AluI        DdeI HinfI      AccI        AccI  ClaI   N1  S
            NlaIII BbvI-             MnlI+MnlI-          AccII      AccII TaqI
                  Fnu4HI                           NspBII          BssHI
                                                    SacII          HhaI
                                                                     HinPI
                                                                     HhaI
                                                                     Hin?I
                                                                            X3

FR-4
        235         245         255         265
GGCCATGGCGGCTAGCGGTTACCGTGAGCTCCTAAGGATCC
 G  H  G  A  S  G  V  T  V  S  S  •  G  S
   aIV    HaeII       AluI DdeI BamHI
   au961  HhaI             BanII MstII NlaIV
   HaeIII HinPI                  Bsp1286    Sau3A
   NcoI   NheI                   HgiAI      XhoII
   NlaIII                        SacI
   StyI

```
         10         20         30         40         50         60         70
GAATTCATGGCTGACAACAAATTCAACAAGGAACAGCAGAACCGTTCTACGAGATCTTGCACCTGCCGAACCTG
 E  F  M  A  D  N  K  F  N  K  E  Q  Q  N  A  F  Y  E  I  L  H  L  P  N  L
EcoRI                               MluI              BglII    BspMI+
                                    XmnI 85         95        105        115        125        135        145
AACGAAGAGCAGCGTAACGGCTTCATCCAAAGCTTGAAAGACGACCCGTCTCAGAGCGCTAACCTGCTGGCAGAG
 N  E  E  Q  R  N  G  F  I  Q  S  L  K  D  D  P  S  Q  S  A  N  L  L  A  E
                            HindIII                          BspMI+
                                                             Eco47III 160        170        180        190        200        210        220
GCCAAGAAACTGAACGACGCTCAGGCGCCGAAGAGTGATCCCGAAGTTCAACTGCAGCAGTCTGGTCCTGAATTG
 A  K  K  L  N  D  A  Q  A  P  K  S  D  P  E  V  Q  L  Q  Q  S  G  P  E  L
                        NarI                        PstI 235        245        255        265        275        285        295
GTTAAACCTGGCGCCTCTGTGCGCATGTCCTGCAAATCCTCTGGTTACATTTTCACCGACTTCTACATGAATTGG
 V  K  P  G  A  S  V  R  M  S  C  K  S  S  G  Y  I  F  T  D  F  Y  M  N  W
           NarI FspI 310        320        330        340        350        360        370
GTTCGCCAGTCTCATGGTAAGTCTCTAGACTACATCGGGTACATTCCCATACTCCTGGGGTTACCGGCTACAAC
 V  R  Q  S  H  G  K  S  L  D  Y  I  G  Y  I  S  P  Y  S  G  V  T  G  Y  N
           BstXI              XbaI                   PflMI           BstEII 385        395        405        415        425        435        445
CAGAAGTTTAAAGGTAAGGCCACCTTACTGTCGACAAATCTTCCTGCTTACATGGAGCTGCGTTCTTTG
 Q  K  F  K  G  K  A  T  L  L  T  V  D  K  S  S  S  T  A  Y  M  E  L  R  S  L
     DraI                   SalI
```

```
       460        470        480        490        500        510        520
ACCTCTGAGGACTCCGCGGTATACTATTGCGGGGCTCCTCTGGTAACAAATGGGCCATGGATTATTGGGGTCAT
 T  S  E  D  S  A  V  Y  Y  C  A  G  S  S  G  N  K  W  A  M  D  Y  W  G  H
              SacII                                   NcoI 535        545        555        565        575        585        595
GGTGCTAGCGTTACTGTGAGCTCTGGTGGCGGTGGCTCGGGTGGCGGTGGGTCGGGGGGCGGCGGATCCGACGTC
 G  A  S  V  T  V  S  S  G  G  G  G  S  G  G  G  G  S  G  G  G  G  S  D  V
     NheI         SacI                                                BamHI AatII 610        620        630        640        650        660        670
GTTGTTACCCAGACTCCGCTGTCTCTGCCCGTTTCTCTGGGTGACCAGGCTTCTATTTCTTGCCGTCTCTCCCAG
 V  V  T  Q  T  P  L  S  L  P  V  S  L  G  D  Q  A  S  I  S  C  R  S  S  Q
                                           BstEII                          PflM 685        695        705        715        725        735        745
TCTCTGGTCCATTCTAATGGTAACACTTACCTGAACTGGTACCTGCAAAAGGCTGGTCAGTCTCCGAAGCTTCTG
 S  L  V  H  S  N  G  N  T  Y  L  N  W  Y  L  Q  K  A  G  Q  S  P  K  L  L
   BstXI                                    BspMI+                        HindIII
                                            KpnI 760        770        780        790        800        810        820
ATCTACAAAGTCTCTAACCGCTTCTCTGGTGTCCCGGATCGTTTCTCTGGTTCTGGTTCTGGTACTGACTTCACC
 I  Y  K  V  S  N  R  F  S  G  V  P  D  R  F  S  G  S  G  S  G  T  D  F  T 835        845        855        865        875        885        895
CTGAAGATCTCTCGTGTCGAGGCCGAAGACCTGGGTATCTACTTCTGCTCTCAGACTACTCATGTACCGCCGACT
 L  K  I  S  R  V  E  A  E  D  L  G  I  Y  F  C  S  Q  T  T  H  V  P  P  T
    BglII 910        920        930        940
TTTGGTGGTGGCACCAAGCTCGAGATTAAACGTTAACTGCAG
 F  G  G  G  T  K  L  E  I  K  R  *
                 XhoI              HpaI PstI
```

```
        10         20         30         40         50         60
GATCCTGACGTCGTAATGACCCAGACTCCGCTGTCTCTGCCGGTTTCTCTGGGTGACCAG
 D  P  D  V  V  M  T  Q  T  P  L  S  L  P  V  S  L  G  D  Q
   AatII                                              BstEII 70         80         90        100        110        120
GCTTCTATTTCTTGCCGCTCTTCCCAGTCTCTGGTCCATTCTAATGGTAACACTTACCTG
 A  S  I  S  C  R  S  S  Q  S  L  V  H  S  N  G  N  T  Y  L
              PflMI                     BstXI 130        140        150        160        170        180
AACTGGTACCTGCAAAAGGCTGGTCAGTCTCCGAAGCTTCTGATCTACAAAGTCTCTAAC
 N  W  Y  L  Q  K  A  G  Q  S  P  K  L  L  I  Y  K  V  S  N
     BspMI+                       HindIII
     KpnI 190        200        210        220        230        240
CGCTTCTCTGGTGTCCCGGATCGTTTCTCTGGTTCTGGTTCTGGTACTGACTTCACCCTG
 R  F  S  G  V  P  D  R  F  S  G  S  G  S  G  T  D  F  T  L 250        260        270        280        290        300
AAGATCTCTCGTGTCGAGGCCGAAGACCTGGGTATCTACTTCTGCTCTCAGACTACTCAT
 K  I  S  R  V  E  A  E  D  L  G  I  Y  F  C  S  Q  T  T  H
   BglII 310        320        330        340        350        360
GTACCGGCGACTTTTGGTGGTGGCACCAAGCTCGAGATTAAACGTGGATCTGGAGGTGGC
 V  P  F  T  F  G  G  G  T  K  L  E  I  K  R  G  S  G  G  G
                              XhoI 370        380        390        400        410        420
GGATCTGGTGGAGGTGGCTCTGGTGGCGGTGGATCCGAAGTTCAATTGCAGCAGTCTGGT
 G  S  G  G  G  G  S  G  G  G  G  S  E  V  Q  L  Q  Q  S  G
                                BamHI
```

FIG. 6B-2

```
        430       440       450       460       470       480
CCTGAATTGGTTAAACCTGGGGCGCCTCTGTGCGGCCATGTCCTGCAAATCCTCTGGGTACATT
 P  E  L  V  K  P  G  A  S  V  R  M  S  C  K  S  S  G  Y  I
                    NarI              FspI 490       500       510       520       530       540
TTCACCGACTTCTACATGAATTGGGTTCGCCAGTCTCATGGTAAGTCTCTAGACTACATC
 F  T  D  F  Y  M  N  W  V  R  Q  S  H  G  K  S  L  D  Y  I
                                BstXI              XbaI 550       560       570       580       590       600
GGGTACATTTCCCCATACTCTGGGGTTACCGGCTACAACCAGAAGTTTAAAGGTAAGGCG
 G  Y  I  S  P  Y  S  G  V  T  G  Y  N  Q  K  F  K  G  K  A
              PflMI       BstEII                  DraI 610       620       630       640       650       660
ACCCTTACTGTCGACAAATCTTCCTCAACTGCTTACATGGAGCTGCGTTCTTTGACCTCT
 T  L  T  V  D  K  S  S  S  T  A  Y  M  E  L  R  S  L  T  S
              SalI 670       680       690       700       710       720
GAGGACTCCGCGGTATACTATTGCGCGGGCTCCTCTGGTAACAAATGGGCCATGGATTAT
 E  D  S  A  V  Y  Y  C  A  G  S  S  G  N  K  W  A  M  D  Y
              SacII                                NcoI 730       740       750       760
TGGGGTCATGGTGCTAGCGGTTACTGTGAGCTCTTAACTGCAG
 W  G  H  G  A  S  V  T  V  S  S  *
```

FIG. 9A-1

```
         10         20         30         40         50         60
GAAGTTCAACTGGAGCAGTCTGGTCCTGGATTGGTTCGACCTTCCCAGACTCTGTCCCTG
 E  V  Q  L  E  Q  S  G  P  G  L  V  R  P  S  Q  T  L  S  L 70         80         90        100        110        120
ACCTGCACATCCTCTGGGTACACATTTCACCGACTTCTACATGAATTGGGTTCGCCAGCCT
 T  C  T  S  S  G  Y  T  F  T  D  F  Y  M  N  W  V  R  Q  P
BspMI+                                                BstXI 130        140        150        160        170        180
CCTGGTCGGGGGTCTAGAGACTACATCGGTTACATTTCCCCATACTCTGGGTTACCGGCTAC
 P  G  R  G  L  D  Y  I  G  Y  I  S  P  Y  S  G  V  T  G  Y
            XbaI                       PflMI        BstEII 190        200        210        220        230        240
AACCAGAAGTTTAAAGGTAAGGCGACCCTTCTCGTGTCAACAAATCTAAGAACCAGGCTTCC
 N  Q  K  F  K  G  K  A  T  L  L  V  N  K  S  K  N  Q  A  S
         DraI 250        260        270        280        290        300
CTGCGGCTGTCTTCTGTGACCGCTGCGGACACCGCGGTATACTATTGCGCGGGCTCCTCT
 L  R  L  S  S  V  T  A  A  D  T  A  V  Y  Y  C  A  G  S  S
                                    SacII 310        320        330        340        350        360
GGTAACAAATGGGCCATGGATTATTGGGGTCAGGGTTCTCTGGTTACTGTGAGCTCTGGT
 G  N  K  W  A  M  D  Y  W  G  Q  G  S  L  V  T  V  S  S  G
               NcoI                                SacI 370        380        390        400        410        420
GGCGGTGGTTCGGGTGGCGGTGGTTCGGGCGGATCCGACGTCGTTATGACCCAG
 G  G  G  S  G  G  G  G  S  G  G  G  S  D  V  V  M  T  Q
                             BamHI AatII
```

```
        430         440         450         460         470         480
CCTCCGTCGGTTTCGGGGGCTCCTGGTCAGCGGGTTACTATTTCTGCCGCTCTCCCAG
 P  P  S  V  S  G  A  P  G  Q  R  V  T  I  S  C  R  S  S  Q
                                                          PflM 490         500         510         520         530         540
TCTCTGGTCCATTCTAATGGTAACACTTACCTGAACTGGTACCAGCAACTGCCTGGTACG
 S  L  V  H  S  N  G  N  T  Y  L  N  W  Y  Q  Q  L  P  G  T
 I  BstXI                               KpnI 550         560         570         580         590         600
GCTCCGAAGCTTCTGATCTACAAAGTCTCTAACCGCTTCTCTGGTGTCCCGGATCGTTTC
 A  P  K  L  L  I  Y  K  V  S  N  R  F  S  G  V  P  D  R  F
       HindIII 610         620         630         640         650         660
TCTGGTTCTGGTTCTGGTACTGACTTCACCCTGGCGATCACTGGTCTCCAGGCCGAAGAC
 S  G  S  G  S  G  T  D  F  T  L  A  I  T  G  L  Q  A  E  D 670         680         690         700         710         720
GAGGCTGACTACTTCTGCTCTCAGACTACTCATGTACCGCCGACTTTTGGTGGTGGCACC
 E  A  D  Y  F  C  S  Q  T  T  H  V  P  P  T  F  G  G  G  T 730         740         750
AAGCTCACGGTTCTGCGTTAACTGCAG
 K  L  T  V  L  R  *  L  Q
              HpaI PstI
```

```
               10         20         30         40         50         60
         GAATTCGAAGTTCAACTGCAGCAGTCTGGTCCTGAATTGGTTAAACCTGGGGCGCCTCTGTG
          E  F  E  V  Q  L  Q  Q  S  G  P  E  L  V  K  P  G  A  S  V
           AsuII   PstI                            NarI            Fs
         EcoRI 70         80         90        100        110        120
         CGCATGTCCTGCAAATCCTCTGGGTACACCTTCACCAACTATTACATTCACTGGCTTAAG
          R  M  S  C  K  S  S  G  Y  T  F  T  N  Y  Y  I  H  W  L  K
         pI                                                         AflII 130        140        150        160        170        180
         CAGTCTCATGGTAAGTCTCTAGAGTCGGTTGGATTACCCGGGTAATGGTAACACT
          Q  S  H  G  K  S  L  E  W  I  G  W  I  Y  P  G  N  G  N  T
                          XbaI                    SmaI 190        200        210        220        230        240
         AAGTACAATGAGAACTTAAAGGTAAGGCGACCCTACTGTCGACAAATCTTCCTCAACT
          K  Y  N  E  N  F  K  G  K  A  T  L  T  V  D  K  S  S  S  T
                          DraI                  SalI 250        260        270        280        290        300
         GCTTACATGGAGCTGCGTTCTTGACCCTGAGGACTCCGCGGTATACTATTGCGCCGCGT
          A  Y  M  E  L  R  S  L  T  S  E  D  S  A  V  Y  Y  C  A  R
                                              SacII          BssHII 310        320        330        340        350        360
         TACACTCATTATTACTTCGATTATTGGGGCCATGGCCTAGCGTTACCGTGAGCTCTGGT
          Y  T  H  Y  Y  F  D  Y  W  G  H  G  A  S  V  T  V  S  S  G
                                        NcoI  NheI        SacI 370        380        390        400        410        420
         GGCGGTGGCTCGGGCGGTGGTGGGTCGGGTGGCGGCGGATCCGACGTCGTTATGACCCAG
          G  G  G  S  G  G  G  G  S  G  G  G  G  S  D  V  V  M  T  Q
                                              BamHI AatII
```

```
                430          440          450          460          470          480
ACTCCGGCTGTCTCTGCCGGTTCTCTGGGTGACCAGGCTTCTATTTCTTGCCGCTCTCC
 T  P  L  S  L  P  V  S  L  G  D  Q  A  S  I  S  C  R  S  S
                                      BstEII 490          500          510          520          530          540
CAGTCTATCGTCCATTCTAATGGTAACTTACCTGGAGTGGTACCTGCAAAAGGCTGGT
 Q  S  I  V  H  S  N  G  N  T  Y  L  E  W  Y  L  Q  K  A  G
         BstXI                                     BspMI+
                                                   KpnI 550          560          570          580          590          600
CAGTCTCCGAAGCTTCTGATCTACAAAGTCTCTAACCGCTTCTCTGGTGTCCCGGATCGT
 Q  S  P  K  L  L  I  Y  K  V  S  N  R  F  S  G  V  P  D  R
             HindIII 610          620          630          640          650          660
TTCTCTGGTTCTGGTACTGACTTCACCCTGAAGATCTCTCGTGTCGAGGCCGAG
 F  S  G  S  G  T  D  F  T  L  K  I  S  R  V  E  A  E
                                       BglII 670          680          690          700          710          720
GATCTGGGTATCTACTACTGCTTCCAAGGGTCTCATGTACCGTGGACTTTCGGCGGTGGG
 D  L  G  I  Y  Y  C  F  Q  G  S  H  V  P  W  T  F  G  G  G 730          740          750
ACCAAGCTCGAGATTAAACGTTAACTGCAG
 T  K  L  E  I  K  R  *  L  Q
     XhoI              HpaI PstI
```

```
         10         20         30         40         50         60
GATCCCGAGGTTATGCTGGTTGAATCTGGTGGAGTACTGATGGAACCTGGTGGGTCCCTG
 D  P  E  V  M  L  V  E  S  G  G  V  L  M  E  P  G  G  S  L
                                 ScaI              EcoO 70         80         90        100        110        120
AAGCTGAGCTGTGCTGCGTCTAGCGGCTTCACGTTCTCTCGTTACGCCATGTCTTGGGTCCGT
 K  L  S  C  A  A  S  G  F  T  F  S  R  Y  A  M  S  W  V  R
 EspI      NheI                                    PflMI 130        140        150        160        170        180
CAGACTCCGGAGAAGCGTCTAGAGTGGGTCGCGGACGATATCTTCTGGTGGTTCTCACACG
 Q  T  P  E  K  R  L  E  W  V  A  T  I  S  S  G  G  S  H  T
           BspMII     XbaI     NruI     EcoRV 190        200        210        220        230        240
CAGACTCCAGACAGTGTGAAGGGTCGATTCACGATCTCTCGAGACAACGGCTAAGAACACG
 Q  T  P  D  S  V  K  G  R  F  T  I  S  R  D  N  A  K  N  T
                                        XhoI 250        260        270        280        290        300
TTGTACCTGCAAATGTCTTCTCTACGTAGTGAAGATACTGCTATGTACTACTGTGCACGT
 L  Y  L  Q  M  S  S  L  R  S  E  D  T  A  M  Y  Y  C  A  R
 BspMI+              SnaBI                              ApaLI 310        320        330        340        350        360
CCTCCACTGATCTCACTAGTTGCTGATTATGCCATGGATTATTGGGGTCATGGTGCTAGC
 P  P  L  I  S  L  V  A  D  Y  A  M  D  Y  W  G  H  G  A  S
             SpeI              NcoI                     NheI 370        380        390        400        410        420
GTTACTGTGAGCTCTGGTGGCGGTGGGCTCGGTGGCTCGGGTGGCGGCGGGATCG
 V  T  V  S  S  G  G  G  G  S  G  G  S  G  G  G  G  S
       SacI
```

```
                  430       440       450       460       470       480
         GATATCGTTATGACTCAGTCTCCATAAGTTCATGTCCACTTCTGTTGGTGACCGTGTTTCT
          D  I  V  M  T  Q  S  H  K  F  M  S  T  S  V  G  D  R  V  S
         EcoRV                                            BstEII 490       500       510       520       530       540
         ATCACTTGTAAGGCCAGCCAGGATGTGGGTGCTGCTATCGCATGGTATCAGCAGAAGCCC
          I  T  C  K  A  S  Q  D  V  G  A  A  I  A  W  Y  Q  Q  K  P
                              PflMI                               Sma 550       560       570       580       590       600
         GGGCAGTCTCCTAAGCTGCTGATCTACTGGGCGTCGACTCGTCATACTGGTGTCCCGGAT
          G  Q  S  P  K  L  L  I  Y  W  A  S  T  R  H  T  G  V  P  D
                                          SalI 610       620       630       640       650       660
         CGTTTCACTGGGTCCGGATCAGGTACTGATTTCACTCTGACTATTTCGAACGTTCAGTCT
          R  F  T  G  S  G  S  G  T  D  F  T  L  T  I  S  N  V  Q  S
                  BspMII                                 AsuII 670       680       690       700       710       720
         CGTTTCACTGGCTGATTACTTCTGCCAGCAATATTCCGGGTACCCCTCTGACTTTCGGTGCC
          D  D  L  A  D  Y  F  C  Q  Q  Y  S  G  Y  P  L  T  F  G  A
                                      SspI        KpnI              Nae 730       740       750
         GGCACTAAACTCGAGCTGAAGTAACTGCAG
          G  T  K  L  E  L  K  *
          I      XhoI               PstI
```

```
         10         20         30         40         50         60
GATCCCGAGGTTATGCTGGTTGAATCTGGTGGAGTACTGATGGAACCTGGTGGGTCCCTG
 D  P  E  V  M  L  V  E  S  G  G  V  L  M  E  P  G  G  S  L
                                    ScaI                EcoO 70         80         90        100        110        120
AAGCTGAGCTGTGCTGCTAGCGGCTTCACGTTCTCTCGTTACGCCATGTCTTGGGTCCGT
 K  L  S  C  A  A  S  G  F  T  F  S  R  Y  A  M  S  W  V  R
 EspI         NheI                              PflMI 130        140        150        160        170        180
CAGACTCCGGAGAAGCGTCTAGAGTGGGTCGCGACGATATCTTCTGGTGGTTCGAACACT
 Q  T  P  E  K  R  L  E  W  V  A  T  I  S  S  G  G  S  N  T
         BspMI    XbaI       NruI  EcoRV                  AsuII 190        200        210        220        230        240
TACTATCCAGACAGTGTGAAGGGTCGATTCACGATTCTCGAGACAACGCTAAGAACACG
 Y  Y  P  D  S  V  K  G  R  F  T  I  S  R  D  N  A  K  N  T
                                            XhoI 250        260        270        280        290        300
TTGTACCTGCAAATGTCTTCTCTACGTAGTGAAGATACTGCTATGTACTACTGTGCACGT
 L  Y  L  Q  M  S  S  L  R  S  E  D  T  A  M  Y  Y  C  A  R
 BspMI+                   SnaBI                           ApaLI 310        320        330        340        350        360
CCTCCACTGATCTCCACTAGTTGCTGATTATGCCATGGATTATTGGGGTCATGGTGCTAGC
 P  P  L  I  S  L  V  A  D  Y  A  M  D  Y  W  G  H  G  A  S
              SpeI                   NcoI                      NheI 370        380        390        400        410        420
GTTACTGTGAGCTCGGTGGGCGGTGGCGGTTCGGGTGGCGGCTCCGGTGGGCGGCGGATCG
 V  T  V  S  S  G  G  G  G  S  G  G  G  G  S  G  G  G  G  S
         SacI
```

```
        430           440           450           460           470           480
GATATCGTTATGACTCAGTCTCATAAGTTCATGTCCACTTCTGTTGGTGACCGTGTTCT
 D   I   V   M   T   Q   S   H   K   F   M   S   T   S   V   G   D   R   V   S
EcoRV                                                       BstEII 490           500           510           520           530           540
ATCACTTGTAAGGCCAGCCAGGATGTGGGTGCTGCTATCGCATGGTATCAGCAGAAGCCC
 I   T   C   K   A   S   Q   D   V   G   A   A   I   A   W   Y   Q   Q   K   P
                    PflMI                                                    Sma 550           560           570           580           590           600
GGGCAGTCTCCTAAGCTGCTGATCTACTGGGCGTCGACTCGTCATACTGGTGTCCCGGAT
 G   Q   S   P   K   L   L   I   Y   W   A   S   T   R   H   T   G   V   P   D
                                       SalI 610           620           630           640           650           660
CGTTTCACTGGGTCCGGATCAGGTACTGATTTCACTCTGACTATTCGAACGTTCAGTCT
 R   F   T   G   S   G   S   G   T   D   F   T   L   T   I   S   N   V   Q   S
          BspMII                                              AsuII 670           680           690           700           710           720
GATGACCTGGCTGATTACTTCTGCCAGCAATATTCCGGGTACCCTCTGACTTTCGGTGCC
 D   D   L   A   D   Y   F   C   Q   Q   Y   S   G   Y   P   L   T   F   G   A
                                       SspI        KpnI                    Nae 730           740           750
GGCACTAAACTCGAGCTGAAGTAACTGCAG
 G   T   K   L   E   L   K   *
 I       XhoI              PstI
```

FIG. 9E-2

```
                                       10
Met Lys Ala Ile Phe Val Leu Lys Gly Ser Leu Asp Arg Asp Leu Asp Ser Arg Leu Asp
ATG AAA GCA ATT TTC GTA CTG AAA GGT TCA CTG GAC AGA GAT CTG GAC TCT CGT CTG GAT
                                                             BglII
                               30                                          40
Leu Asp Val Arg Thr Asp His Lys Asp Leu Ser Asp His Leu Val Leu Val Asp Leu Ala
CTG GAC GTT CGT ACC GAC CAC AAA GAC CTG TCT GAT CAC CTG GTT CTG GTC GAC CTG GCT
                                       BclI                            SalI
                               50                                          60
Arg Asn Asp Leu Ala Arg Ile Val Thr Pro Gly Ser Arg Tyr Val Ala Asp Leu Glu Phe
CGT AAC GAC CTG GCT CGT ATC GTT ACT CCC GGG TCT CGT TAC GTT GCG GAT CTG GAA TTC
                                       SmaI                                EcoRI
Asp
GAT
```

FIG. 10A

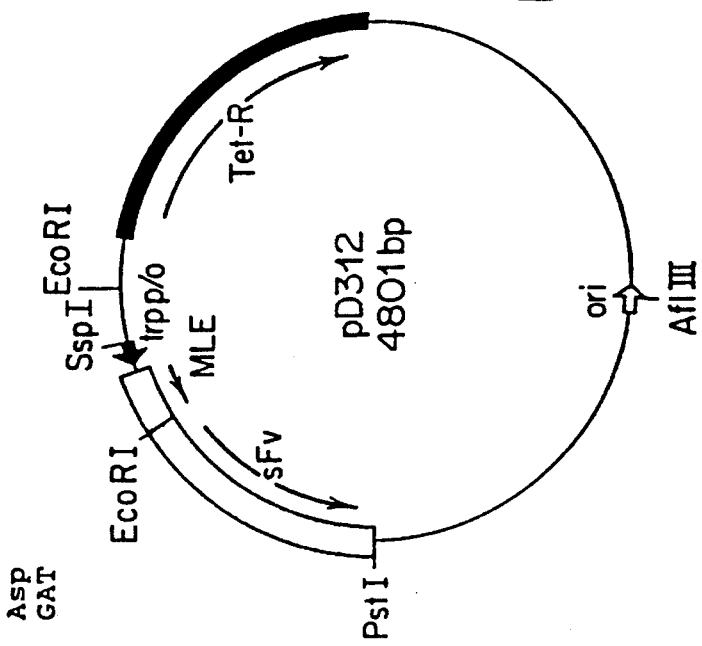

FIG. 10B

```
        10         20         30         40         50         60
GAATTCATGGCTGACAACAAATTCAACAAGGAACAGCAGAACGCGTTCTACGAGATCTTG
  E  F  M  A  D  N  K  F  N  K  E  Q  Q  N  A  F  Y  E  I  L
EcoRI                                    MluI           BglII
                                         XmnI 70         80         90        100        110        120
CACCTGCCGAACCTGAACGAAGAGCAGCGTAACGGCTTCATCCAAAGCTTGAAGGATGAG
  H  L  P  N  L  N  E  E  Q  R  N  G  F  I  Q  S  L  K  D  E
BspMI+                                          HindIII 130        140        150        160        170        180
CCCTCTCAGTCTGCGAATCTGCTAGCGGATGCCAAGAAACTGAACGATGCGCAGGCACCG
  P  S  Q  S  A  N  L  L  A  D  A  K  K  L  N  D  A  Q  A  P
                    NheI                          FspI 190        200        210        220        230        240
AAATCGGATCAGGGGCAATTCATGGCTGACAACAAATTCAACAAGGAACAGCAGAACGCG
  K  S  D  Q  G  Q  F  M  A  D  N  K  F  N  K  E  Q  Q  N  A
                                                    MluI
                                                    XmnI 250        260        270        280        290        300
TTCTACGAGATCTTGCACCTGCCGAACCTGAACGAAGAGCAGCGTAACGGCTTCATCCAA
  F  Y  E  I  L  H  L  P  N  L  N  E  E  Q  R  N  G  F  I  Q
     BglII    BspMI+                                        H 310        320        330        340        350        360
AGCTTGAAGGATGAGCCCTCTCAGTCTGCGAATCTGCTAGCGGATGCCAAGAAACTGAAC
  S  L  K  D  E  P  S  Q  S  A  N  L  L  A  D  A  K  K  L  N
indIII                              NheI 370        380
GATGCGCAGGCACCGAAATCGGATCC                      FIG. 14
  D  A  Q  A  P  K  S  D  P
FspI                BamHI
```

(BABS)-

```
         10        20        30        40        50        60        70
GGATCCGGTAACTCTGACTCTGAATGCCCGCTGAGCCACGACGGGTACTGCCTGCACGACGGTGTTTGCATGTAC
 G  S  G  N  S  D  S  E  C  P  L  S  H  D  G  Y  C  L  H  D  G  V  C  M  Y
BamHI                    BsmI+     EspI 85        95       105       115       125       135       145
ATCGAAGCTCTGGACAAATACGCCATGCAACTGCGTTGTAGGCTACATCGGTGAGCGCTGCCAGTATCGCGATCTG
 I  E  A  L  D  K  Y  A  C  N  C  V  V  G  Y  I  G  E  R  C  Q  Y  R  D  L
                        SphI                                    NruI 160       170
AAATGGTGGGAGCTGCGTTAACTGCAG
 K  W  W  E  L  R  *
                 HpaI PstI
```

(BABS)-

```
          10        20        30        40        50        60
GGATCCGGTGGCGACCCGTCCAAGGACTCCAAAGCTCAGGTTTCTGCTGCCAAGCTGGT
 G  S  G  G  D  P  S  K  D  S  K  A  Q  V  S  A  A  E  A  G
BamHI 70        80        90       100       110       120
ATCACTGGCACCTGGTATAACCAACTGGGGTCGACTTTCATTGTGACCGCTGGTGCCGAC
 I  T  G  T  W  Y  N  Q  L  G  S  T  F  I  V  T  A  G  A  D
                              SalI 130       140       150       160       170       180
GGAGCTCTGACTGGCACCTACGAATCTGCGGTTGGTAACGCAGAATCCCGCTACGTACTG
 G  A  L  T  G  T  Y  E  S  A  V  G  N  A  E  S  R  Y  V  L
 SacI                                                  SnaBI 190       200       210       220       230       240
ACTGGCCGTTATGACTCTGCACCTGCCACCGATGGCTCTGGTACCGCTCTGGGCTGGACT
 T  G  R  Y  D  S  A  P  A  T  D  G  S  G  T  A  L  G  W  T
             BspMI+                KpnI 250       260       270       280       290       300
GTGGCTTGGAAAAACAACTATCGTAATGCGCACAGCGCCACTACGTGGTCTGGCCAATAC
 V  A  W  K  N  N  Y  R  N  A  H  S  A  T  T  W  S  G  Q  Y
                      FspI      DraIII    BalI
                                PflMI          BstXI
```

```
          310       320       330       340       350       360
GTTGGGCGGTGCTGAGGCTCGTATCAACACTCAGTGGCTGTTAACATCCGGCACTACCGAA
 V  G  G  A  E  A  R  I  N  T  Q  W  L  L  T  S  G  T  T  E
                            DraIII          HpaI 370       380       390       400       410       420
GCGAATGCATGGAAATCGACACTAGTCATGACACCTTTACCAAAGTTAAGCCTTCT
 A  N  A  W  K  S  T  L  V  G  H  D  T  F  T  K  V  K  P  S
BsmI+              SpeI
 NsiI 430       440       450       460       470       480
GCTGCTAGCATTGATGCTGCCAAGAAGAAGGCAGGGGTAAACAACGGTAACCCTCTAGACGCT
 A  A  S  I  D  A  A  K  K  K  A  G  V  N  N  G  N  P  L  D  A
    NheI                                    BstEII    XbaI 490       500
GTTCAGCAATAACTGCAG
 V  Q  Q  *
        PstI
```

```
(BABS)-
              10         20         30         40         50         60
         GGATCCGGTGTACGTAGCTCCTCTCCGCACTCCGTCCGATAAGCCGGTTGCTCATGTAGTT
           G  S  G  V  R  S  S  S  R  T  P  S  D  K  P  V  A  H  V  V
         BamHI    SnaBI 70         80         90        100        110        120
         GCTAACCCTCAGGCAGAAGGTCAGCTTCAGTGGCTGAACCGTCGCGCTAACGCCCTGCTG
           A  N  P  Q  A  E  G  Q  L  Q  W  L  N  R  R  A  N  A  L  L
                MstII                                        BglI 130        140        150        160        170        180
         GCAAACGGCGTTGAGCTCCGTGATAACCAGCTCGTGGTACCTTCTGAAGGTCTGTACCTG
           A  N  G  V  E  L  R  D  N  Q  L  V  V  P  S  E  G  L  Y  L
                       SacI            PflMI    KpnI 190        200        210        220        230        240
         ATCTATTCTCAAGTACTGTTCAAGGGTCAAGGGTGCCCGTCGACTCATGTTCTGCTGACT
           I  Y  S  Q  V  L  F  K  G  Q  G  C  P  S  T  H  V  L  L  T
                      ScaI                             SalI 250        260        270        280        290        300
         CACACCATCAGCCGTATTGCTGTATCTTACCAGACCAAAGTTAACCTGCTGAGCGCTATC
           H  T  I  S  R  I  A  V  S  Y  Q  T  K  V  N  L  L  S  A  I
                                                   HpaIBspMI+ Eco47III
                                                          EspI
```

```
       310        320        330        340        350        360
AAGTCTCCGTGCCAGCGTGAAACTCCCGAGGGTGCAGAAGCCGAAACCATGGTATGAACCG
 K  S  P  C  Q  R  E  T  P  E  G  A  E  A  K  P  W  Y  E  P
                                              NcoI 370        380        390        400        410        420
ATCTACCTGGGGTGGGGCGTATTTCAACTGGAGAGAAAGGTGACCGTCTGTCCGCAGAAATCAAC
 I  Y  L  G  G  V  F  Q  L  E  K  G  D  R  L  S  A  E  I  N
                                   BstEII 430        440        450        460        470        480
CGTCCTGACTATCTAGATTTCGCTGAATCTGGCCAGGTTGTACTTCGGTGTATTATCGCACTG
 R  P  D  Y  L  D  F  A  E  S  G  Q  V  Y  F  G  I  I  A  L
           XbaI              BalI

490
TAACTGCAG
 *       PstI
```

(BABS) -

```
         10         20         30         40         50         60
GGATCCGGTGCTGATCAGCTGACTGACGAGCAGATCGCTGAATTAAAGAGGCTTTCTCT
 G  S  G  A  D  Q  L  T  D  E  Q  I  A  E  F  K  E  A  F  S
BamHI     BclIPvuII                            DraI 70         80         90        100        110        120
CTGTTTGACAAAGACGGTGACGGTACCATCACTACCAAAGAGCTCGGCACCGTTATGCGC
 L  F  D  K  D  G  D  G  T  I  T  T  K  E  L  G  T  V  M  R
                        KpnI           SacI                FspI 130        140        150        160        170        180
AGCCTTGGCCAGAACCCGACTGAAGCTGAATTGCAGGACATGATCAACGAAGTCGACGCT
 S  L  G  Q  N  P  T  E  A  E  L  Q  D  M  I  N  E  V  D  A
     BalI                                      BclI     SalI 190        200        210        220        230        240
GACGGTAACGGCACCATCGATTTTCCGGAATTTCTGAACCTGATGGCGCGCAAGATGAAA
 D  G  N  G  T  I  D  F  P  E  F  L  N  L  M  A  R  K  M  K
              ClaI  BspMII                              BssHII
```

```
         250        260        270        280        290        300
GACACTGACTCTGAAGAGGAACTGAAAGAGGCCTTCCGTGTTTTCGACAAAGACGGTAAC
 D  T  D  S  E  E  E  E  L  K  E  A  F  R  V  F  D  K  D  G  N
                              StuI 310        320        330        340        350        360
GGTTTCATCTCGGCCGCTGAACTGCGTCACGTTATGACTAACCTGGGTGAAAAGCTTACT
 G  F  I  S  A  A  E  L  R  H  V  M  T  N  L  G  E  K  L  T
        EagI                                        HindIII 370        380        390        400        410        420
GACGAAGAAGTTGACGAAATGATTCGCGAAGCTGACGTCGATGGTGACGGCCAGGTTAAC
 D  E  E  V  D  E  M  I  R  E  A  D  V  D  G  D  G  Q  V  N
              XmnI        NruI     AatII                HpaI 430        440        450
TACGAAGAGTTCGTTCAGGTTATGATGGCTAAGTAACTGCAG
 Y  E  E  F  V  Q  V  M  M  A  K  *
                                    PstI
```

FIG. 15D-2

FIG. 15E (BABS)—

```
          10         20         30         40         50         60
GGATCCGGTGGAGGCTCTCTGGGCTCTCTGACTATTGCCGAACCGGCAATGATTGCTGAA
 G  S  G  G  G  S  L  G  S  L  T  I  A  E  P  A  M  I  A  E
BamHI                              BglI                    Bsm 70         80         90        100        110        120
TGCAAGACTCGTACCGAAGTCTTCGAGATCTCTCGTCGTCTGATCGATCGCACTAATGCC
 C  K  T  R  T  E  V  F  E  I  S  R  R  L  I  D  R  T  N  A
 I+             BglII                     ClaI              Bs
                                          PvuI 130        140        150        160        170        180
AACTTCCTGGTATGGCCGCCGTGCGAGGTACAACGCTGCTCCGGGTGTTGCAACAAT
 N  F  L  V  W  P  P  C  V  E  V  Q  R  C  S  G  C  N  N
tXI 190        200        210        220        230        240
CGTAACGTTCAATGTGCGACCGACTCAAGTCCAGTGCCTCCGGTCCAAGTCCGCAAAATC
 R  N  V  Q  C  R  P  T  Q  V  Q  L  R  P  V  Q  V  R  K  I
                SalI                      PvuII 250        260        270        280        290        300
GAGATTGTACGTAAGAAAACCGATCTTTAAGAAGGCCACTGTTACTCTGGAAGACCATCTG
 E  I  V  R  K  K  P  I  F  K  K  A  T  V  T  L  E  D  H  L
                SnaBI 310        320        330        340        350
GCATGCAAATGTGAGACTGTAGCGGCCGCCACGTCCAGTTACTTAACTGCAG
 A  C  K  C  E  T  V  A  A  A  R  P  V  T  *    PstI
SphI            EagI
                NotI
```

FIG. 15F-1

(BABS)-

```
         10         20         30         40         50         60
GGATCCGGTATATTCCCCAAACAATATCCCAATTATAAACTTTACCACAGCGGGTGCCACT
 G  S  G  I  F  P  K  Q  Y  P  I  I  N  F  T  T  A  G  A  T
BamHI 70         80         90        100        110        120
GTGCAAAGCTACACAAACTTTATCAGAGCTGTTCCGGGTCGTTTAACAACTGGAGCTGAT
 V  Q  S  Y  T  N  F  I  R  A  V  R  G  R  L  T  T  G  A  D 130        140        150        160        170        180
GTGAGACATGAAATACCAGTGTTGCCAAACAGAGTTGGTTTGCCTATAAACCAACGGTTT
 V  R  H  E  I  P  V  L  P  N  R  V  G  L  P  I  N  Q  R  F 190        200        210        220        230        240
ATTTTAGTTGAACTCTCAAATCATGCAGAGCTTTCTGTTACATTAGCGCTGGATGTCACC
 I  L  V  E  L  S  N  H  A  E  L  S  V  T  L  A  L  D  V  T
                                                  Eco47III 250        260        270        280        290        300
AATGCATATGTGGTCGGCTACCGTGCTGGAAATAGCGCATATTTCTTTCATCCTGACAAT
 N  A  Y  V  V  G  Y  R  A  G  N  S  A  Y  F  F  H  P  D  N
    NdeI
    NsiI
```

```
        310         320         330         340         350         360
CAGGAAGATGCAGAAGCAAATCACTCACTCATCTTTCACTGATGTTCAAAATCGATATACATTC
 Q  E  D  A  E  A  I  T  H  L  F  T  D  V  Q  N  R  Y  T  F
                                                    ClaI 370         380         390         400         410         420
GCCTTTGGTGGTAATTATGATAGACTTGAACAACTTGCTGGTAATCTGAGAGAAAATATC
 A  F  G  G  N  Y  D  R  L  E  Q  L  A  G  N  L  R  E  N  I 430         440         450         460         470         480
GAGTTGGGAAATGGTCCACTAGAGGAGGCTATCTCAGCGCTTTATTATTACAGTACTGGT
 E  L  G  N  G  P  L  E  E  A  I  S  A  L  Y  Y  Y  S  T  G
                                   Eco47III                ScaI 490         500         510         520         530         540
GGCACTCAGCTTCCAACTCTGGCTCGTTCCTTTATAATTTGCATCCAAATGATTTCAGAA
 G  T  Q  L  P  T  L  A  R  S  F  I  I  C  I  Q  M  I  S  E 550         560         570         580         590         600
GCAGCAAGATTCCAATATATTGAGGAGAAATGCGCACGAGAATTAGGTACAACCGGAGA
 A  A  R  F  Q  Y  I  E  G  E  M  R  T  R  I  R  Y  N  R  R
                            FspI                           BglI
```

FIG. 15 F-2

FIG. 15G (BABS)-

```
         10         20         30         40         50         60
GGATCCGGTGCTCCGACTTCTAGCTTCTACTAAGAAAACTCAGCTTCAGCTGGAACACCTG
 G  S  G  A  P  T  S  S  S  T  K  K  T  Q  L  Q  L  E  H  L
BamHI                                         PvuII 70         80         90        100        110        120
CTGCTGGACCTTCAGATGATCCTGAACGGTATCAACAACTACAAGAACCCGAAACTGACT
 L  L  D  L  Q  M  I  L  N  G  I  N  N  Y  K  N  P  K  L  T 130        140        150        160        170        180
CGTATGCTGACTTTCAAATTCTACATGCCGAAGAAAGCTACCGAACTGAAAACACCTTCAG
 R  M  L  T  F  K  F  Y  M  P  K  K  A  T  E  L  K  H  L  Q 190        200        210        220        230        240
TGCCTGGAAGAAGAACTGAAGCCGCTGGAGGAAGTACTGAACCTGGCTCAGTCTAAAAAC
 C  L  E  E  E  L  K  P  L  E  E  V  L  N  L  A  Q  S  K  N
                         ScaI 250        260        270        280        290        300
TTCCACCTGCGTCCGCGTGACCTGATCAGCAACATCAACGTAATCGTTCTAGAACTTAAA
 F  H  L  R  P  R  D  L  I  S  N  I  N  V  I  V  L  E  L  K
                   BclI                        XbaI 310        320        330        340        350        360
GGCTCTGAAACTACCTTCATGTGCGAATACGCTGACGAAACTGCTACCATCGTAGAATTT
 G  S  E  T  T  F  M  C  E  Y  A  D  E  T  A  T  I  V  E  F 370        380        390        400        410        420
CTGAACCGTTGGATCACCTTCTGCCAGTCTATCATCTCTACTCTGACTTAACTGCAG
 L  N  R  W  I  T  F  C  Q  S  I  I  S  T  L  T  *
                                                    PstI
```

FIG. 15 H-1

(BABS)-

```
         10        20        30        40        50        60
GGATCCGGTGCTGACAACAAATTCAACAAGGAACAGCAGAACGCGTTCTACGAGATCTTG
 G  S  G  A  D  N  K  F  N  K  E  Q  Q  N  A  F  Y  E  I  L
BamHI                              MluI              BglII
                                   XmnI 70        80        90       100       110       120
CACCTGCCGAACCTGAACGAAGAGCAGCGTAACGGCTTCATCCAAAGCTTGAAGGATGAG
 H  L  P  N  L  N  E  E  Q  R  N  G  F  I  Q  S  L  K  D  E
BspMI+                                        HindIII 130       140       150       160       170       180
CCCTCTCAGTCTGCGAATCTGCTAGCGGATGCCAAGAAACTGAACGATGCCCAGGCACCG
 P  S  Q  S  A  N  L  L  A  D  A  K  K  L  N  D  A  Q  A  P
                     NheI                            FspI 190       200       210       220       230       240
AAATCGGATCAGGGGCAATTCATGGCTGACAACAAATTCAACAAGGAACAGCAGAACGCG
 K  S  D  Q  G  Q  F  M  A  D  N  K  F  N  K  E  Q  Q  N  A
                                                  MluI
                                                  XmnI
```

```
          250            260            270            280            290            300
TTCTACGAGATCTTCTGCACCTGCCGAACCTGAACGAAGAGCAGCGTAACGGCTTCATCCAA
 F  Y  E  I  L  H  H  L  P  N  L  N  E  E  Q  R  N  G  F  I  Q
       BglII      BspMI+

310            320            330            340            350            360
AGCTTGAAGGATGAGCCCTCTCAGTCTGCGAATCTGCTAGCGGATGCCAAGAAAACTGAAC
 S  L  K  D  E  P  S  Q  S  A  N  L  L  A  D  A  K  K  L  N
 indIII                                   NheI 370            380
GATGCGCAGGCACCGAAATAACTGCAG
 D  A  Q  A  P  K  *
 FspI                PstI
```

POLYPEPTIDE LINKERS FOR PRODUCTION OF BIOSYNTHETIC PROTEINS

The United States Government has rights in this application pursuant to small business innovation research grant numbers SSS-4 R43 CA39870-01 and SSS-4 2 R44 CA39870-02.

REFERENCE TO RELATED APPLICATIONS

This application is a continuation of U.S. Ser. No. 07/955,399 filed Oct. 1, 1992, now U.S. Pat. No. 5,258,498, which is a continuation of U.S. Ser. No. 07/342,449 filed Jan. 23, 1989, now abandoned, which is a continuation-in-part of U.S. Ser. No. 07/052,800, filed May 21, 1987, now abandoned. Related applications include: U.S. Ser. No. 07/636,765 filed Jan. 2 1991, now U.S. Pat. No. 5,091,513, which is a divisional of U.S. Ser. No. 07/213,671, filed Jun. 30, 1988 and now U.S. Pat. No. 5,132,405, which is a continuation of U.S. Ser. No. 07/052,800 filed May 21, 1987, now abandoned; and U.S. Ser. No. 08/139,901 filed Oct. 19, 1993, which is a continuation of U.S. Ser. No. 07/850,228 filed Mar. 12, 1992, which is a divisional of U.S. Ser. No. 07/213,671, filed Jun. 30, 1988, now U.S. Pat. No. 5,132,405, which is a continuation of U.S. Ser. No. 07/52,800 filed May 21, 1987, now abandoned.

BACKGROUND OF THE INVENTION

This invention relates to novel compositions of matter, hereinafter called targeted multifunctional proteins, useful, for example, in specific binding assays, affinity purification, biocatalysis, drug targeting, imaging, immunological treatment of various oncogenic and infectious diseases, and in other contexts. More specifically, this invention relates to biosynthetic proteins expressed from recombinant DNA as a single polypeptide chain comprising plural regions, one of which has a structure similar to an antibody binding site, and an affinity for a preselected antigenic determinant, and another of which has a separate function, and may be biologically active, designed to bind to ions, or designed to facilitate immobilization of the protein. This invention also relates to the binding proteins per se, and methods for their construction.

There are five classes of human antibodies. Each has the same basic structure (see FIG. 1), or multiple thereof, consisting of two identical polypeptides called heavy (H) chains (molecularly weight approximately 50,000 d) and two identical light (L) chains (molecular weight approximately 25,000 d). Each of the five antibody classes has a similar set of light chains and a distinct set of heavy chains. A light chain is composed of one variable and one constant domain, while a heavy chain is composed of one variable and three or more constant domains. The combined variable domains of a paired light and heavy chain are known as the Fv region, or simply "Fv". The Fv determines the specificity of the immunoglobulin, the constant regions have other functions.

Amino acid sequence data indicate that each variable domain comprises three hypervariable regions or loops, sometimes called complementarity determining regions or "CDRs" flanked by four relatively conserved framework regions or "FRs" (Kabat et. al., *Sequences of Proteins of Immunological Interest* [U.S. Department of Health and Human Services, third edition, 1983, fourth edition, 1987]). The hypervariable regions have been assumed to be responsible for the binding specificity of individual antibodies and to account for the diversity of binding of antibodies as a protein class.

Monoclonal antibodies have been used both as diagnostic and therapeutic agents. They are routinely produced according to established procedures by hybridomas generated by fusion of mouse lymphoid cells with an appropriate mouse myeloma cell line.

The literature contains a host of references to the concept of targeting bioactive substances such as drugs, toxins, and enzymes to specific points in the body to destroy or locate malignant cells or to induce a localized drug or enzymatic effect. It has been proposed to achieve this effect by conjugating the bioactive substance to monoclonal antibodies (see, e.g., Vogel, *Imunoconjugates, Antibody Conjugates in Radioimaging and Therapy of Cancer*, 1987, N.Y., Oxford University Press; and Ghose et al. (1978) J. Natl. Cancer Inst. 61:657–676,). However, non-human antibodies induce an immune response when injected into humans. Human monoclonal antibodies may alleviate this problem, but they are difficult to produce by cell fusion techniques since, among other problems, human hybridomas are notably unstable, and removal of immunized spleen cells from humans is not feasible.

Chimetic antibodies composed of human and non-human amino acid sequences potentially have improved therapeutic value as they presumably would elicit less circulating human antibody against the non-human immunoglobulin sequences. Accordingly, hybrid antibody molecules have been proposed which consist of amino acid sequences from different mammalian sources. The chimeric antibodies designed thus far comprise variable regions from one mammalian source, and constant regions from human or another mammalian source (Morrison et al. (1984) Proc. Natl. Acad. Sci. U.S.A., 81:5851–6855; Neuberger et al. (1984) Nature 312:604–608; Sahagan et al. (1986) J. Immunol 137:1066–1074; EPO application nos. 84302368.0, Genentech; 85102665.8, Research Development Corporation of Japan; 85305604.2, Stanford; P.C.T. application no. PCT/GB85/00392, Celltech Limited).

It has been reported that binding function is localized to the variable domains of the antibody molecule located at the amino terminal end of both the heavy and light chains. The variable regions remain noncovalently associated (as $V_H V_L$ dimers, termed Fv regions) even after proteolytic cleavage from the native antibody molecule, and retain much of their antigen recognition and binding capabilities (see, for example, Inbar et al., Proc. Natl. Acad. Sci. U.S.A. (1972) 69:2659–2662; Hochman et. al. (1973) Biochem. 12:1130–1135; and (1976) Biochem. 15:2706–2710; Sharon and Givol (1976) Biochem. 15:1591–1594; Rosenblatt and Haber (1978) Biochem. 17:3877–3882; Ehrlich et al. (1980) Biochem. 19:4091–40996). Methods of manufacturing two-chain Fv substantially free of constant region using recombinant DNA techniques are disclosed in U.S. Pat. No. 4,642,334 and corresponding published specification EP 088,994.

SUMMARY OF THE INVENTION

In one aspect the invention provides a single chain multifunctional biosynthetic protein expressed from a single gene derived by recombinant DNA techniques. The protein comprises a biosynthetic antibody binding site (BABS) comprising at least one protein domain capable of binding to a preselected antigenic determinant. The amino acid sequence of the domain is homologous to at least a portion of the sequence of a variable region of an immunoglobulin molecule capable of binding the preselected antigenic determinant. Peptide bonded to the binding site is a polypeptide consisting of an effector protein having a conformation suitable for biological activity in a mammal, an amino acid sequence capable of sequestering ions, or an amino acid sequence capable of selective binding to a solid support.

In another aspect, the invention provides biosynthetic binding site protein comprising a single polypeptide chain defining two polypeptide domains connected by a polypeptide linker. The amino acid sequence of each of the domains comprises a set of complementarity determining regions (CDRs) interposed between a set of framework regions (FRs), each of which is respectively homologous with at least a portion of the CDRs and FRS from an immunoglobulin molecule. At least one of the domains comprises a set of CDR amino acid sequences and a set of FR amino acid sequences at least partly homologous to different immunoglobulins. The two polypeptide domains together define a hybrid synthetic binding site having specificity for a preselected antigen, determined by the selected CDRs.

In still another aspect, the invention provides biosynthetic binding protein comprising a single polypeptide chain defining two domains connected by a polypeptide linker. The amino acid sequence of each of the domains comprises a set of CDRs interposed between a set of FRs, each of which is respectively homologous with at least a portion of the CDRs and FRs from an immunoglobulin molecule. The linker comprises plural, peptide-bonded amino acids defining a polypeptide of a length sufficient to span the distance between the C terminal end of one of the domains and N terminal end of the other when the binding protein assumes a conformation suitable for binding. The linker comprises hydrophilic amino acids which together preferably constitute a hydrophilic sequence. Linkers which assume an unstructured polypeptide configuration in aqueous solution work well. The binding protein is capable of binding to a preselected antigenic site, determined by the collective tertiary structure of the sets of CDRs held in proper conformation by the sets of FRs. Preferably, the binding protein has a specificity at least substantially identical to the binding specificity of the immunoglobulin molecule used as a template for the design of the CDR regions. Such structures can have a binding affinity of at least $10^6$, $M^{-1}$, and preferably $10^8$ $M^{-1}$.

In preferred aspects, the FRs of the binding protein are homologous to at least a portion of the FRs from a human immunoglobulin, the linker spans at least about 40 angstroms; a polypeptide spacer is incorporated in the multifunctional protein between the binding site and the second polypeptide; and the binding protein has an affinity for the preselected antigenic determinant no less than two orders of magnitude less than the binding affinity of the immunoglobulin molecule used as a template for the CDR regions of the binding protein. The preferred linkers and spacers are cysteine-free. The linker preferably comprises amino acids having unreactive side groups, e.g., alanine and glycine. Linkers and spacers can be made by combining plural consecutive copies of an amino acid sequence, e.g., $(Gly_4 Ser)_3$. The invention also provides DNAs encoding these proteins and host cells harboring and capable of expressing these DNAs.

As used herein, the phrase biosynthetic antibody binding site or BABS means synthetic proteins expressed from DNA derived by recombinant techniques. BABS comprise biosynthetically produced sequences of amino acids defining polypeptides designed to bind with a preselected antigenic material. The structure of these synthetic polypeptides is unlike that of naturally occurring antibodies, fragments thereof, e.g., Fv, or known synthetic polypeptides or "chimeric antibodies" in that the regions of the BABS responsible for specificity and affinity of binding, (analogous to native antibody variable regions) are linked by peptide bonds, expressed from a single DNA, and may themselves be chimetic, e.g., may comprise amino acid sequences homologous to portions of at least two different antibody molecules. The BABS embodying the invention are biosynthetic in the sense that they are synthesized in a cellular host made to express a synthetic DNA, that is, a recombinant DNA made by ligation of plural, chemically synthesized oligonucleotides, or by ligation of fragments of DNA derived from the genome of a hybridoma, mature B cell clone, or a cDNA library derived from such natural sources. The proteins of the invention are properly characterized as "binding sites" in that these synthetic molecules are designed to have specific affinity for a preselected antigenic determinant. The polypeptides of the invention comprise structures patterned after regions of native antibodies known to be responsible for antigen recognition.

Accordingly, it is an object of the invention to provide novel multifunctional proteins comprising one or more effector proteins and one or more biosynthetic antibody binding sites, and to provide DNA sequences which encode the proteins. Another object is to provide a generalized method for producing biosynthetic antibody binding site polypeptides of any desired specificity.

BRIEF DESCRIPTION OF THE DRAWINGS

The foregoing and other objects of this invention, the various features thereof, as well as the invention itself, may be more fully understood from the following description, when read together with the accompanying drawings.

FIG. 1A is a schematic representation of an intact IgG antibody molecule containing two light chains, each consisting of one variable and one constant domain, and two heavy chains, each consisting of one variable and three constant domains. FIG. 1B is a schematic drawing of the structure of Fv proteins (and DNA encoding them) illustrating $V_H$ and $V_L$ domains, each of which comprises four framework (FR) regions and three complementarity determining (CDR) regions. Boundaries of CDRs are indicated, by way of example, for monoclonal 26-10, a well known and characterized murine monoclonal specific for digoxin.

FIG. 3 discloses five amino acid sequences (heavy chains) in single letter code lined up vertically to facilitate understanding of the invention. Sequence 1 is the known native sequence Of $V_H$ from murine monoclonal glp-4 (anti-lysozyme). Sequence 2 is the known native sequence of $V_H$ from murine monoclonal 26-10 (anti-digoxin). Sequence 3 is a BABS comprising the FRs from 26-10 $V_H$ and the CDRs from glp-4 $V_H$. The CDRs are identified in lower case letters; restriction sites in the DNA used to produce chimetic sequence 3 are also identified. Sequence 4 is the known native sequence of $V_H$ from human myeloma antibody NEWM. Sequence 5 is a BABS comprising the FRs from NEWM $V_H$ and the CDRs from glp-4 $V_H$, i.e., illustrates a "humanized" binding site having a human framework but an affinity for lysozlrme similar to murine glp-4.

FIGS. 4A–4F are the synthetic nucleic acid sequences and encoded amino acid sequences of (4A) the heavy chain variable domain of murine anti-digoxin monoclonal 26-10; (4B) the light chain variable domain of murine anti-digoxin monoclonal 26-10; (4C) a heavy chain variable domain of a BABS comprising CDRs of glp-4 and FRs of 26-10; (4D) a light chain variable region of the same BABS; (4E) a heavy chain variable region of a BABS comprising CDRs of glp-4 and FRs of NEWM; and (4F) a light chain variable region comprising CDRs of glp-4 and FRs of NEWM. Delineated are FRs, CDRs, and restriction sites for endonuclease digestion, most of which were introduced during design of the DNA.

FIG. 5 is the nucleic acid and encoded amino acid sequence of a host DNA ($V_H$) designed to facilitate insertion of CDRs of choice. The DNA was designed to have unique 6-base sites directly flanking the CDRs so that relatively small oligonucleotides defining portions of CDRs can be readily inserted, and to have other sites to facilitate manipulation of the DNA to optimize binding properties in a given construct. The framework regions of the molecule correspond to murine FRs (FIG. 4A).

FIGS. 6A and 6B are multifunctional proteins (and DNA encoding them) comprising a single chain BABS with the specificity of murine monoclonal 26-10, linked through a spacer to the FB fragment of protein A, here fused as a leader, and constituting a binding site for Fc. The spacer comprises the 11 C-terminal amino acids of the FB followed by Asp-Pro (a dilute acid cleavage site). The single chain BABS comprises sequences mimicking the $V_H$ and $V_L$ (6A) and the $V_L$ and $V_H$ (6B) of murine monoclonal 26-10. The $V_L$ in construct 6A is altered at residue 4 where valine replaces methionine present in the parent 26-10 sequence. These constructs contain binding sites for both Fc and digoxin. Their structure may be summarized as;

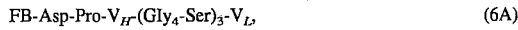

FB-Asp-Pro-$V_H$-(Gly$_4$-Ser)$_3$-$V_L$,                    (6A)

and

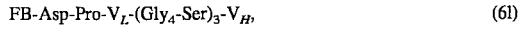

FB-Asp-Pro-$V_L$-(Gly$_4$-Ser)$_3$-$V_H$,                    (6I)

where (Gly$_4$-Ser)$_3$ is a polypeptide linker.

In FIGS. 4A–4E and 6A and 6B the amino acid sequence of the expression products start after the GAATTC sequences, which codes for an EcoRI splice site, translated as Glu-Phe on the drawings.

Figure 2A:
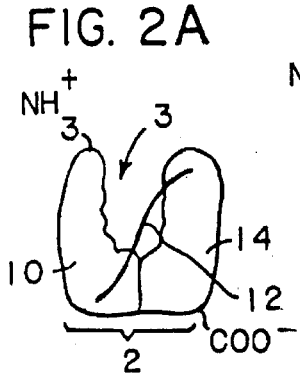
FIG. 2A–2E are schematic representations of some of the classes of reagents constructed in accordance with the invention, each of which comprises a biosynthetic antibody binding site.
Figure 2B:
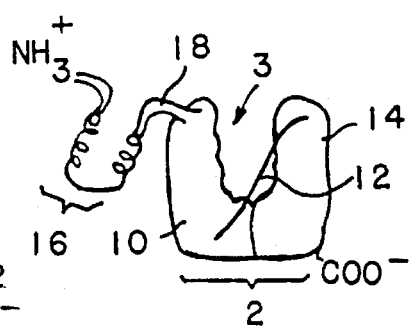
Figure 7A:
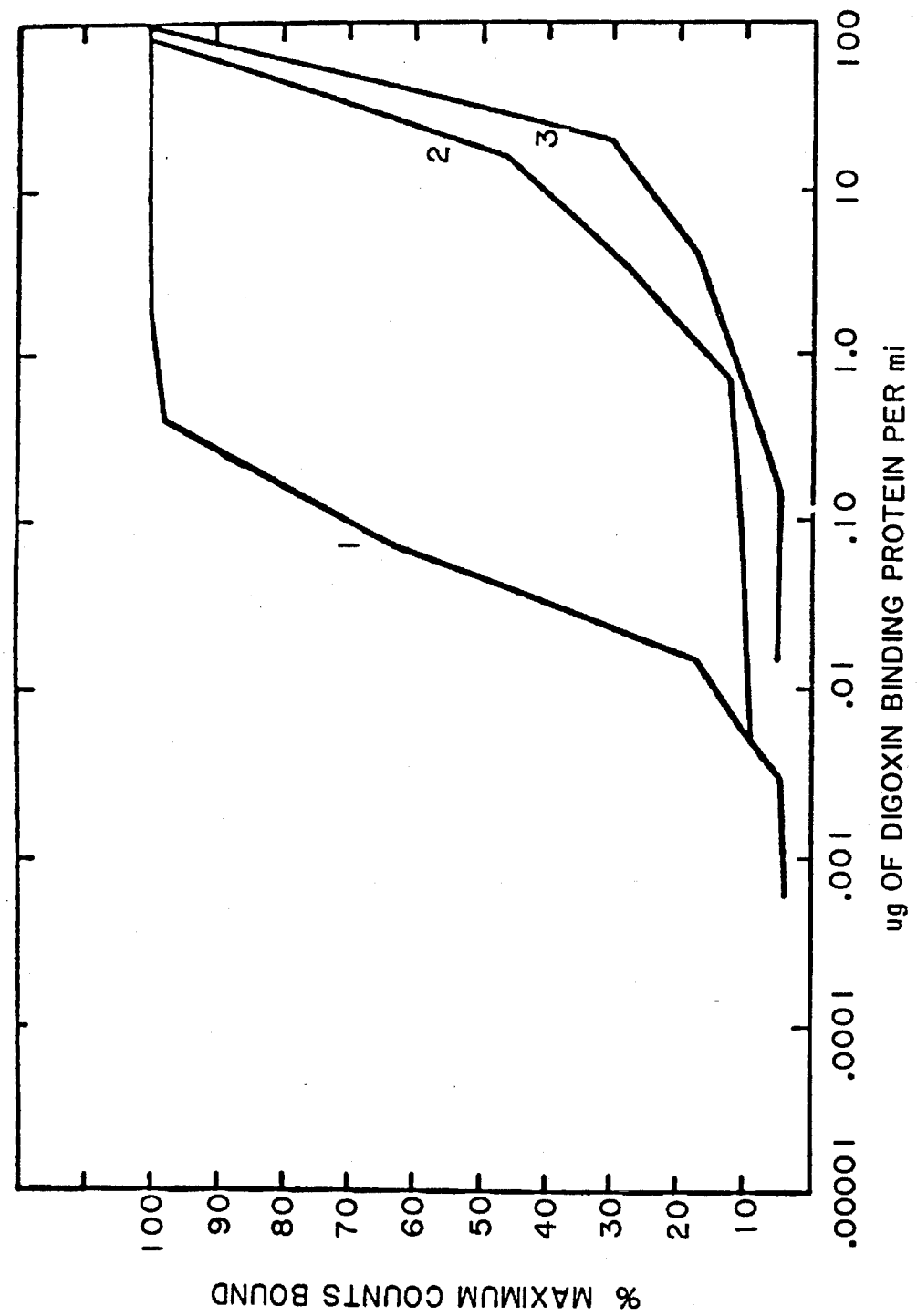
Figure 7B:
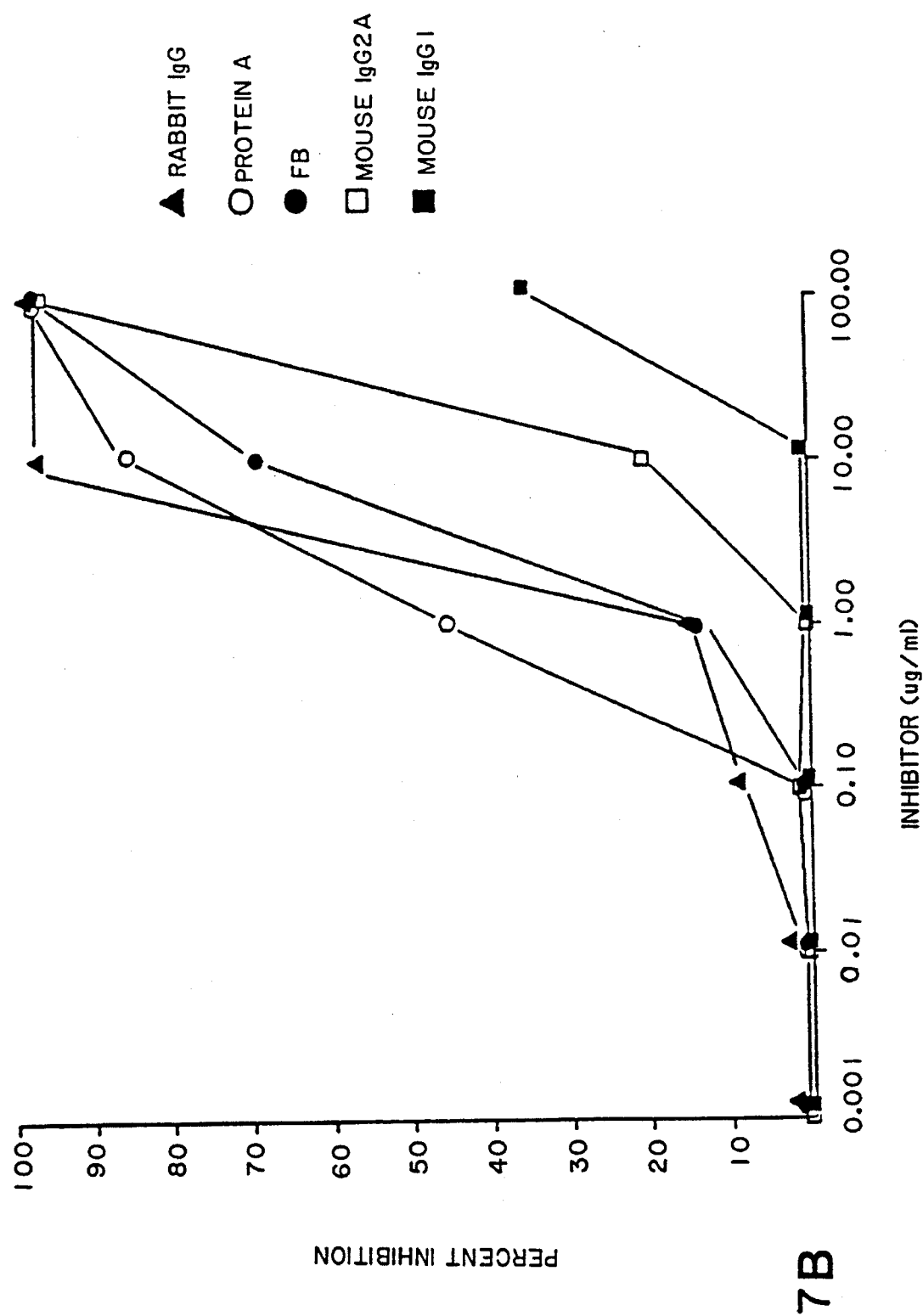

FIG. 7A is a graph of percent of maximum counts bound of radioiodinated digoxin versus concentration of binding protein adsorbed to the plate comparing the binding of native 26-10 (curve 1) and the construct of FIG. 6A and FIG. 2B renatured using two different procedures (curves 2 and 3). FIG. 7B is a graph demonstrating the bifunctionality of the FB-(26-10) BABS adhered to microtiter plates through the specific binding of the binding site to the digoxin-BSA coat on the plate. FIG. 7B shows the percent inhibition of $^{125}$I-rabbit-IgG binding to the FB domain of the FB BABS by the addition of IgG, protein A, FB, murine IgG2a, and murine IgG1.

Figures 8, 9C:
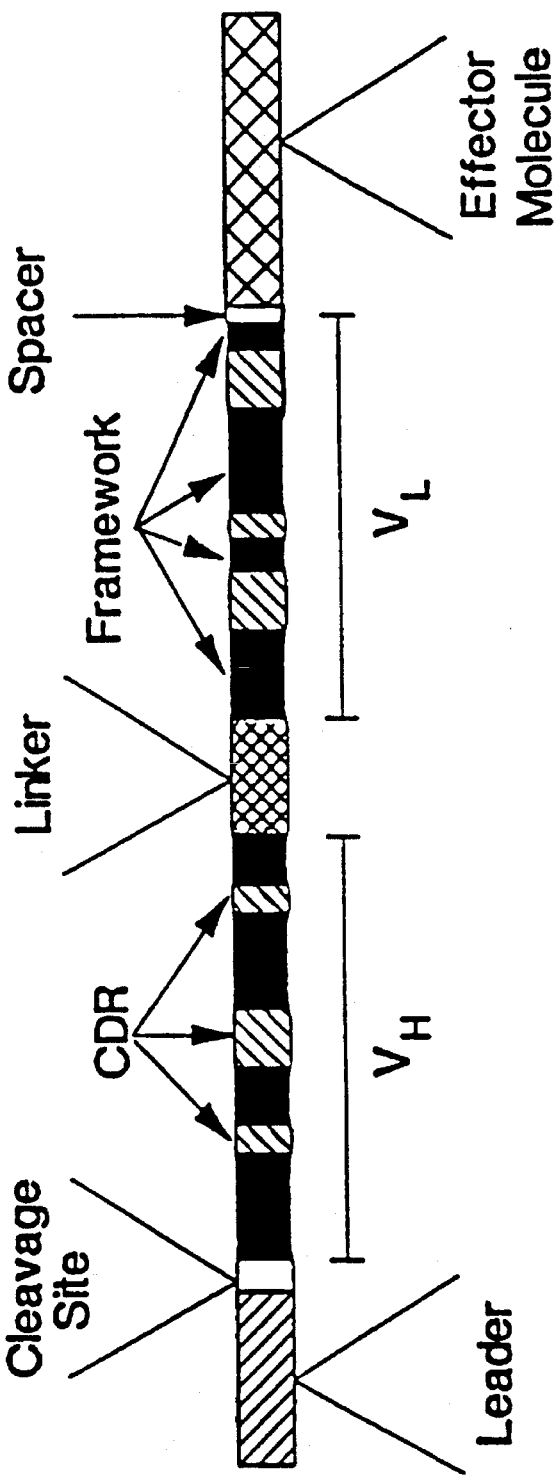

FIG. 8 is a schematic representation of a model assembled DNA sequence encoding a multifunctional biosynthetic protein comprising a leader peptide (used to aid expression and thereafter cleaved), a binding site, a spacer, and an effector molecule attached as a trailer sequence.

FIGS. 9A–9E are exemplary synthetic nucleic acid sequences and corresponding encoded amino acid sequences of binding sites of different specificities: (A) FRs from NEWM and CDRs from 26-10 having the digoxin specificity of murine monoclonal 26-10; (B) FRs from 26-10, and CDRs from G-loop-4 (glp-4) having lysozyme specificity; (C) FRs and CDRs from MOPC-315 having dinitrophenol (DNF) specificity; (D) FRs and CDRs from an anti-CEA monoclonal antibody; (E) FRs in both $V_H$ and $V_L$ and CDR$_1$ and CDR$_3$ in $V_H$, and CDR$_1$, CDR$_2$, and CDR$_3$ in $V_L$ from an anti-CEA monoclonal antibody; CDR$_2$ in $V_H$ is a CDR$_2$ consensus sequence found in most immunoglobul in $V_H$ regions.

FIG. 10A is a schematic representation of the DNA and amino acid sequence of a leader peptide (MLE) protein with corresponding DNA sequence and some major restriction sites. FIG. 10B shows the design of an expression plasmid used to express MLE-BABS (26-10). During construction of the gene, fusion partners were joined at the EcoR1 site that is shown as part of the leader sequence. The pBR322 plasmid, opened at the unique SspI and PstI sites, was combined in a 3-part ligation with an SspI to EcoRI fragment bearing the trp promoter and MLE leader and with an EcoRI to PstI fragment carrying the BABS gene. The resulting expression vector confers tetracycline resistance on positive transformants.

Figure 11:
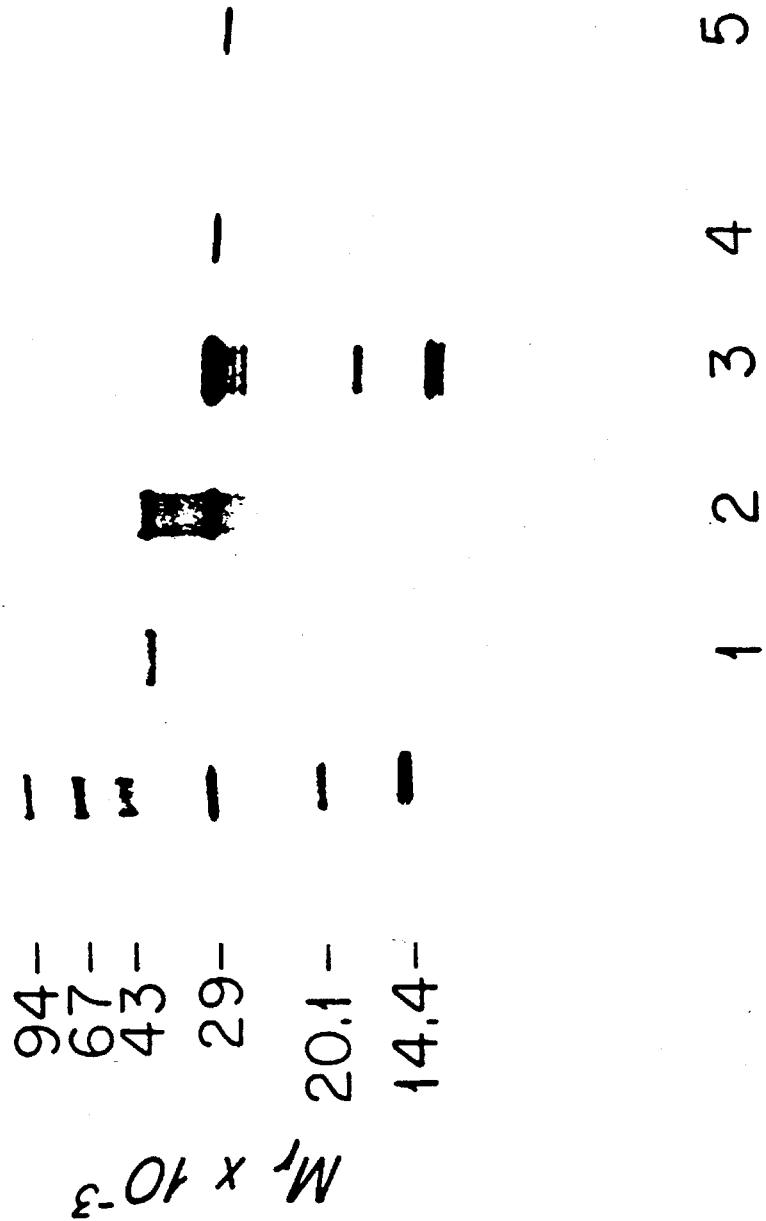

FIG. 11 is an SDS-polyacrylamide gel (15%) of the (26-10) BABS at progressive stages of purification. Lane 0 shows low molecular weight standards; lane i is the MLE-BABS fusion protein; lane 2 is an acid digest of this material; lane 3 is the pooled DE-52 chromatographed protein; lanes 4 and 5 are the same oubain-Sepharose pool of single chain BABS except that lane 4 protein is reduced and lane 5 protein is unreduced.

Figure 12:
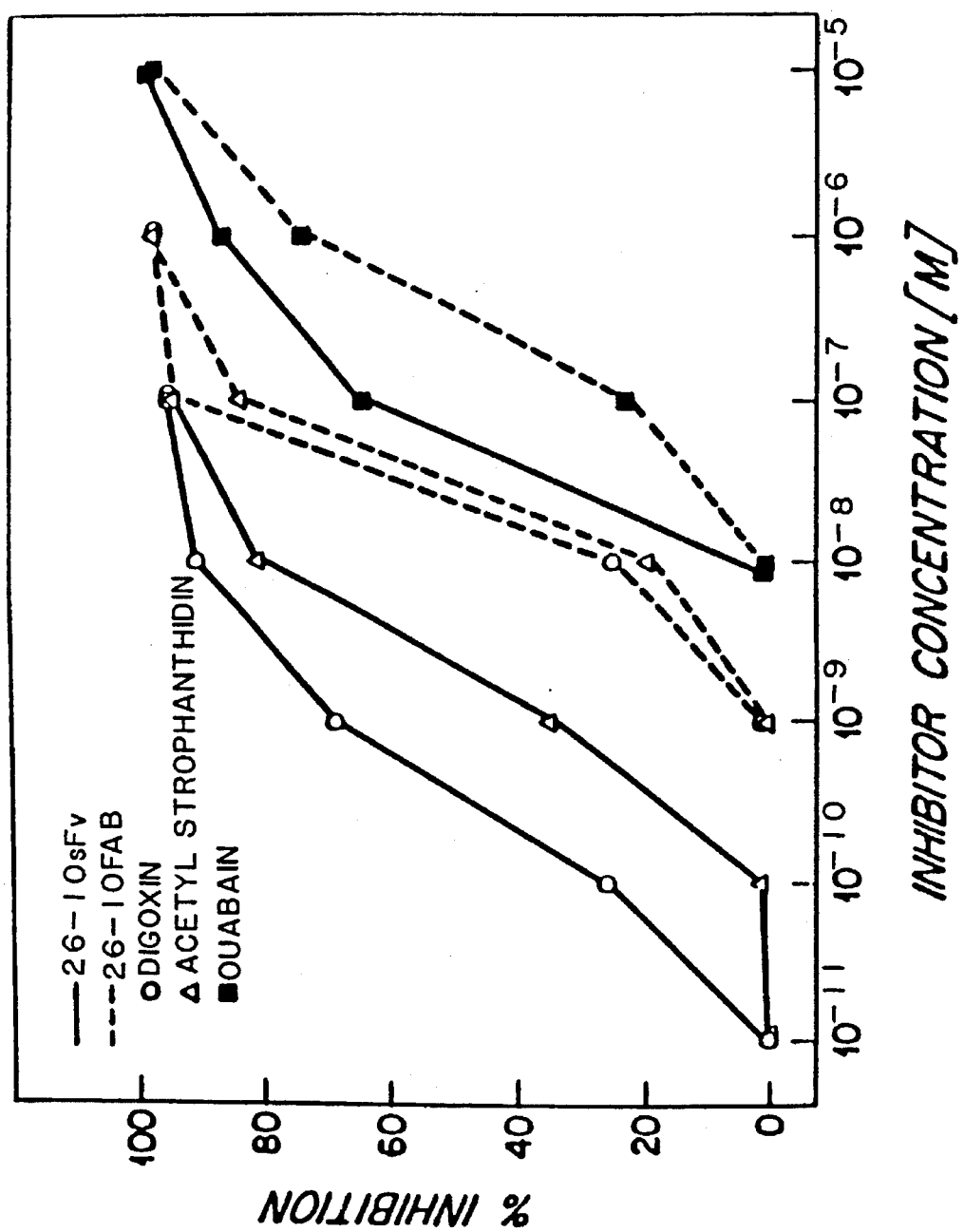

FIG. 12 shows inhibition curves for 26-10 BABS and 26-10 Fab species, and indicates the relative affinities of the antibody fragment for the indicated cardiac glycosides.

Figure 13A:
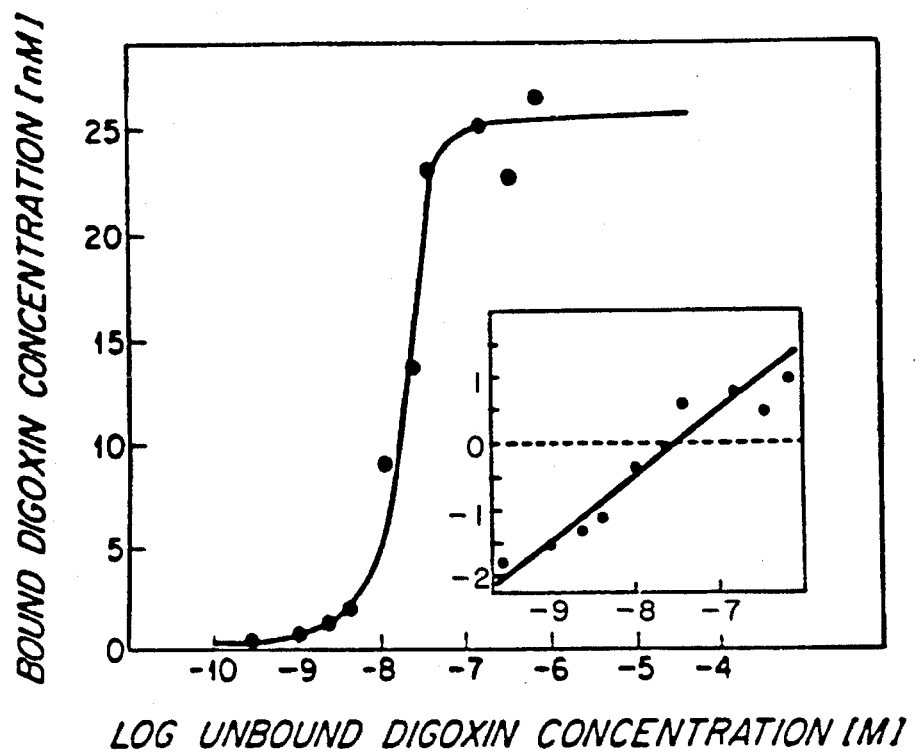
Figure 13B:
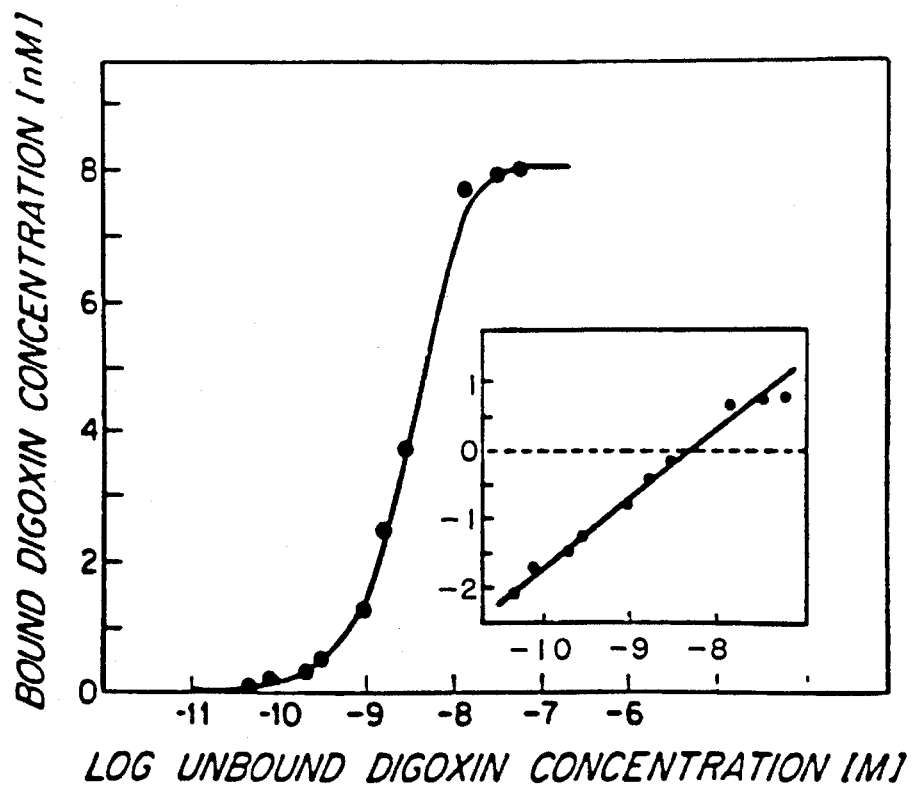

FIGS. 13A and 13B are plots of digoxin binding curves. (A) shows 26-10 BABS binding isotherm and Sips plot (inset), and (B) shows 26-10 Fab binding isotherm and Sips plot (inset).

FIG. 14 is a nucleic acid sequence and corresponding amino acid sequence of a modified FB dimer leader sequence and various restriction sites.

FIGS. 15A–15H are nucleic acid sequences and corresponding amino acid sequences of biosynthetic multifunctional proteins including a single chain BABS and various biologically active protein trailers linked via a spacer sequence. Also indicated are various endonuclease digestion sites. The trailing sequences are (A) epidermal growth factor (EGF); (B) streptavidin; (C) tumor necrosis factor (TNF); (D) calmodulin; (E) platelet derived growth factor-beta (PDGF-beta); (F) ricin; and interleukin-2, and (H) an FB-FB dimer.

DESCRIPTION

The invention will first be described in its broadest overall aspects with a more detailed description following.

A class of novel biosynthetic, bi or multifunctional proteins has now been designed and engineered which comprise biosynthetic antibody binding sites, that is, "BABS" or biosynthetic polypeptides defining structure capable of selective antigen recognition and preferential antigen binding, and one or more peptide-bonded additional protein or polypeptide regions designed to have a preselected property. Examples of the second region include amino acid sequences designed to sequester ions, which makes the protein suitable for use as an imaging agent, and sequences designed to facilitate immobilization of the protein for use in affinity chromatography and solid phase immunoassay.

Another example of the second region is a bioactive effector molecule, that is, a protein having a conformation suitable for biological activity, such as an enzyme, toxin, receptor, binding site, growth factor, cell differentiation factor, lymphokine, cytokine, hormone, or anti-metabolite. This invention features synthetic, multifunctional proteins comprising these regions peptide bonded to one or more biosynthetic antibody binding sites, synthetic, single chain proteins designed to bind preselected antigenic determinants with high affinity and specificity, constructs containing multiple binding sites linked together to provide multipoint antigen binding and high net affinity and specificity, DNA encoding these proteins prepared by recombinant techniques, host cells harboring these DNAs, and methods for the production of these proteins and DNAs.

The invention requires recombinant production of single chain binding sites having affinity and specificity for a predetermined antigenic determinant. This technology has been developed and is disclosed herein. In view of this disclosure, persons skilled in recombinant DNA technology, protein design, and protein chemistry can produce such sites which, when disposed in solution, have high binding constants (at least $10^6$, preferably $10^8$ $M^{-1}$,) and excellent specificity The design of the BABS is based on the observation that three subregions of the variable domain of each of the heavy and light chains of native immunoglobulin molecules collectively are responsible for antigen recognition and binding. Each of these subregions, called herein "complementarity determining regions" or CDRs, consists of one of the hypervariable regions or loops and of selected amino acids or amino acid sequences disposed in the framework regions or FRs which flank that particular hypervariable region. It has now been discovered that FRs from diverse species are effective to maintin CDRs from diverse other species in proper conformation so as to achieve true immunochemical binding properties in a biosynthetic protein. It has also been discovered that biosynthetic domains mimicking the structure of the two chains of an immunoglobulin binding site may be connected by a polypeptide linker while closely approaching, retaining, and often improving their collective binding properties.

The binding site region of the multifunctional proteins comprises at least one, and preferably two domains, each of which has an amino acid sequence homologous to portions of the CDRs of the variable domain of an immunoglobulin light or heavy chain, and other sequence homologous to the FRs of the variable domain of the same, or a second, different immunoglobulin light or heavy chain. The two domain binding site construct also includes a polypeptide linking the domains. Polypeptides so constructed bind a specific preselected antigen determined by the CDRs held in proper conformation by the FRs and the linker. Preferred structures have human FRs, i.e., mimic the amino acid sequence of at least a portion of the framework regions of a human immunoglobulin, and have linked domains which together comprise structure mimicking a $V_H$-$V_L$ or $V_L$-$V_H$ immunoglobulin two-chain binding site. CDR regions of a mammalian immunoglobulin, such as those of mouse, rat, or human origin are preferred. In one preferred embodiment, the biosynthetic antibody binding site comprises FRs homologous with a portion of the FRs of a human immunoglobulin and CDRs homologous with CDRs from a mouse or rat immunoglobulin. This type of chimetic polypeptide displays the antigen binding specificity of the mouse or rat immunoglobulin, while its human framework minimizes human immune reactions. In addition, the chimetic polypeptide may comprise other amino acid sequences. It may comprise, for example, a sequence homologous to a portion of the constant domain of an immunoglobulin, but preferably is free of constant regions (other than FRs).

The binding site region(s) of the chimetic proteins are thus single chain composite polypeptides comprising a structure which in solution behaves like an antibody binding site. The two domain, single chain composite polypeptide has a structure patterned after tandem $V_H$ and $V_L$ domains, but with the carboxyl terminal of one attached through a linking amino acid sequence to the amino terminal of the other. The linking amino acid sequence may or may not itself be antigenic or biologically active. It preferably spans a distance of at least about 40A, i.e., comprises at least about 14 amino acids, and comprises residues which together present a hydrophilic, relatively unstructured region. Linking amino acid sequences having little or no secondary structure work well. Optionally, one or a pair of unique amino acids or amino acid sequences recognizable by a site specific cleavage agent may be included in the linker. This permits the $V_H$ and $V_L$-like domains to be separated after expression, or the linker to be excised after refolding of the binding site.

Either the amino or carboxyl terminal ends (or both ends) of these chimetic, single chain binding sites are attached to an amino acid sequence which itself is bioactive or has some other function to produce a bifunctional or multifunctional protein. For example, the synthetic binding site may include a leader and/or trailer sequence defining a polypeptide having enzymatic activity, independent affinity for an antigen different from the antigen to which the binding site is directed, or having other functions such as to provide a convenient site of attachment for a radioactive ion, or to provide a residue designed to link chemically to a solid support. This fused, independently functional section of protein should be distinguished from fused leaders used simply to enhance expression in prokaryotic host cells or yeasts. The multifunctional proteins also should be distinguished from the "conjugates" disclosed in the prior art comprising antibodies which, after expression, are linked chemically to a second moiety.

Often, a series of amino acids designed as a "spacer" is interposed between the active regions of the multifunctional protein. Use of such a spacer can promote independent refolding of the regions of the protein. The spacer also may include a specific sequence of amino acids recognized by an endopeptidase, for example, endogenous to a target cell (e.g., one having a surface protein recognized by the binding site) so that the bioactive effector protein is cleaved and released at the target. The second functional protein preferably is present as a trailer sequence, as trailers exhibit less of a tendency to interfere with the binding behavior of the BABS.

The therapeutic use of such "self-targeted" bioactive proteins offers a number of advantages over conjugates of immunoglobulin fragments or complete antibody molecules: they are stable, less immunogenic and have a lower molecular weight; they can penetrate body tissues more rapidly for purposes of imaging or drug delivery because of their smaller size; and they can facilitate accelerated clearance of targeted isotopes or drugs. Furthermore, because design of such structures at the DNA level as disclosed herein permits ready selection of bioproperties and specificities, an essentially limitless combination of binding sites and bioactive proteins is possible, each of which can be refined as disclosed herein to optimize independent activity at each region of the synthetic protein. The synthetic proteins can be expressed in procaryotes such as *E. coli*, and thus are less costly to produce than immunoglobulins or fragments thereof which require expression in cultured animal cell lines.

The invention thus provides a family of recombinant proteins expressed from a single piece of DNA, all of which have the capacity to bind specifically with a predetermined antigenic determinant. The preferred species of the proteins comprise a second domain which functions independently of the binding region. In this aspect the invention provides an array of "self-targeted" proteins which have a bioactive function and which deliver that function to a locus determined by the binding site's specificity. It also provides biosynthetic binding proteins having attached polypeptides suitable for attachment to immobilization matrices which may be used in affinity chromatography and solid phase immunoassay applications, or suitable for attachment to ions, e.g., radioactive ions, which may be used for in vivo imaging.

The successful design and manufacture of the proteins of the invention depends on the ability to produce biosynthetic binding sites, and most preferably, sites comprising two domains mimicking the variable domains of immunoglobulin connected by a linker.

As is now well known, Fv, the minimum antibody fragment which contains a complete antigen recognition and binding site, consists of a dimer of one heavy and one light chain variable domain in noncovalent association (FIG. 1A). It is in this configuration that the three complementarity determining regions of each variable domain interact to define an antigen binding site on the surface of the $V_H$-$V_L$ dimer. Collectively, the six complementarity determining regions (see FIG. 1B) confer antigen binding specificity to the antibody. FRs flanking the CDRs have a tertiary structure which is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although at a lower affinity than an entire binding site (Painter et al. (1972) Biochem. 11:1327–1337).

This knowledge of the structure of immunoglobulin proteins has now been exploited to develop multifunctional fusion proteins comprising biosynthetic antibody binding sites and one or more other domains.

The structure of these biosynthetic proteins in the region which impart the binding properties to the protein is analogous to the Fv region of a natural antibody. It comprises at least one, and preferably two domains consisting of amino acids defining $V_H$ and $V_L$-like polypeptide segments connected by a linker which together form the tertiary molecular structure responsible for affinity and specificity. Each domain comprises a set of amino acid sequences analogous to immunoglobulin CDRs held in appropriate conformation by a set of sequences analogous to the framework regions (FRs) of an Fv fragment of a natural antibody.

The term CDR, as used herein, refers to amino acid sequences which together define the binding affinity and specificity of the natural Fv region of a native immunoglobulin binding site, or a synthetic polypeptide which mimics this function. CDRs typically are not wholly homologous to hypervariable regions of natural Fvs, but rather also may include specific amino acids or amino acid sequences which flank the hypervariable region and have heretofore been considered framework not directly determinitive of complementarity. The term FR, as used herein, refers to amino acid sequences flanking or interposed between CDRs.

The CDR and FR polypeptide segments are designed based on sequence analysis of the Fv region of preexisting antibodies or of the DNA encoding them. In one embodiment, the amino acid sequences constituting the FR regions of the BABS are analogous to the FR sequences of a first preexisting antibody, for example, a human IgG. The amino acid sequences constituting the CDR regions are analogous to the sequences from a second, different preexisting antibody, for example, the CDRs of a murine IgG. Alternatively, the CDRs and FRs from a single preexisting antibody from, e.g., an unstable or hard to culture hybridoma, may be copied in their entirety.

Practice of the invention enables the design and biosynthesis of various reagents, all of which are characterized by a region having affinity for a preselected antigenic determinant. The binding site and other regions of the biosynthetic protein are designed with the particular planned utility of the protein in mind. Thus, if the reagent is designed for intravascular use in mammals, the FR regions may comprise amino acids similar or identical to at least a portion of the framework region amino acids of antibodies native to that mammalian species. On the other hand, the amino acids comprising the CDRs may be analogous to a portion of the amino acids from the hypervariable region (and certain flanking amino acids) of an antibody having a known affinity and specificity, e.g., a murine or rat monoclonal antibody.

Other sections of native immunoglobulin protein structure, e.g., $C_H$ and $C_L$, need not be present and normally are intentionally omitted from the biosynthetic proteins. However, the proteins of the invention normally comprise additional polypeptide or protein regions defining a bioactive region, e.g., a toxin or enzyme, or a site onto which a toxin or a remotely detectable substance can be attached.

The invention thus can provide intact biosynthetic antibody binding sites analogous to $V_H$-$V_L$ dimers, either noncovalently associated, disulfide bonded, or preferably linked by a polypeptide sequence to form a composite $V_H$-$V_L$ or $V_L$-$V_H$ polypeptide which may be essentially free of antibody constant region. The invention also provides proteins analogous to an independent $V_H$ or $V_L$ domain, or dimers thereof. Any of these proteins may be provided in a form linked to, for example, amino acids analogous or homologous to a bioactive molecule such as a hormone or toxin.

Connecting the independently functional regions of the protein is a spacer comprising a short amino acid sequence whose function is to separate the functional regions so that they can independently assume their active tertiary conformation. The spacer can consist of an amino acid sequence present on the end of a functional protein which sequence is not itself required for its function, and/or specific sequences engineered into the protein at the DNA level.

The spacer generally may comprise between 5 and 25 residues. Its optimal length may be determined using constructs of different spacer lengths varying, for example, by units of 5 amino acids. The specific amino acids in the spacer can vary. Cysteines should be avoided. Hydrophilic amino acids are preferred. The spacer sequence may mimic the sequence of a hinge region of an immunoglobulin. It may also be designed to assume a structure, such as a helical structure. Proteolytic cleavage sites may be designed into the spacer separating the variable region-like sequences from other pendant sequences so as to facilitate cleavage of intact BABS, free of other protein, or so as to release the bioactive protein in vivo.

FIGS. 2A–2E illustrate five examples of protein structures embodying the invention that can be produced by following the teaching disclosed herein. All are characterized by a biosynthetic polypeptide defining a binding site 3, comprising amino acid sequences comprising CDRs and FRs, often derived from different immunoglobulins, or sequences homologous to a portion of CDRs and FRs from different immunoglobulins. FIG. 2A depicts a single chain construct comprising a polypeptide domain 10 having an amino acid sequence analogous to the variable region of an immunoglobulin heavy chain, bound through its carboxyl end to a polypeptide linker 12, which in turn is bound to a polypeptide domain 14 having an amino acid sequence analogous to the variable region of an immunoglobulin light chain. Of course, the light and heavy chain domains may be in reverse order. Alternatively, the binding site may comprise two substantially homologous amino acid sequences which are both analogous to the variable region of an immunoglobulin heavy or light chain.

The linker 12 should be long enough (e.g., about 15 amino acids or about 40 Å to permit the chains 10 and 14 to assume their proper conformation. The linker 12 may comprise an amino acid sequence homologous to a sequence identified as "self" by the species into which it will be introduced, if drug use is intended. For example, the linker may comprise an amino acid sequence patterned after a hinge region of an immunoglobulin. The linker preferably comprises hydrophilic amino acid sequences. It may also comprise a bioactive polypeptide such as a cell toxin which is to be targeted by the binding site, or a segment easily labelled by a radioactive reagent which is to be delivered, e.g., to the site of a tumor comprising an epitope recognized by the binding site. The linker may also include one or two built-in cleavage sites, i.e., an amino acid or amino acid sequence susceptible to attack by a site specific cleavage agent as described below. This strategy permits the $V_H$ and $V_L$-like domains to be separated after expression, or the linker to be excised after folding while retaining the binding site structure in non-covalent association. The amino acids of the linker preferably are selected from among those having relatively small, unreactive side chains. Alanine, serine, and glycine are preferred.

Generally, the design of the linker involves considerations similar to the design of the spacer, excepting that binding properties of the linked domains are seriously degraded if the linker sequence is shorter than about 20Å in length, i.e., comprises less than about 10 residues. Linkers longer than the approximate 40Å distance between the N terminal of a native variable region and the C-terminal of its sister chain may be used, but also potentially can diminish the BABS binding properties. Linkers comprising between 12 and 18 residues are preferred. The preferred length in specific constructs may be determined by varying linker length first by units of 5 residues, and second by units of 1–4 residues after determining the best multiple of the pentameric starting units.

Figure 2C:
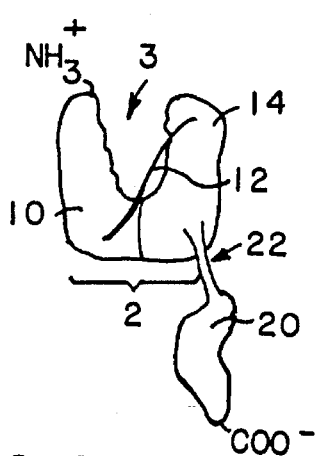
Figure 2D:
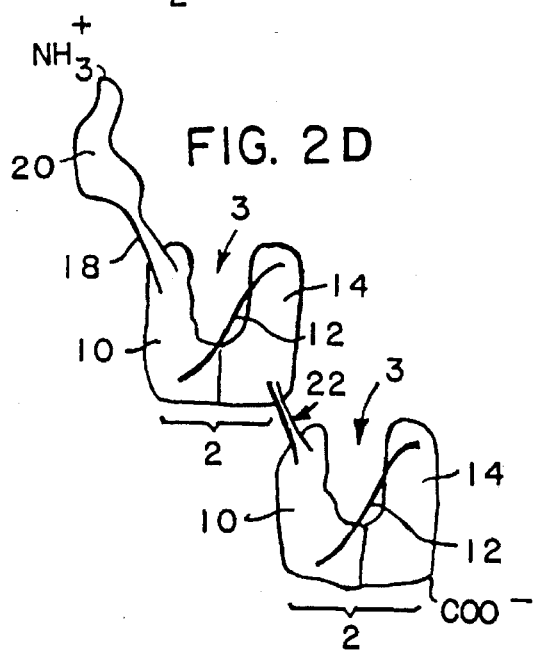

Additional proteins or polypeptides may be attached to either or both the amino or carboxyl termini of the binding site to produce multifunctional proteins of the type illustrated in FIGS. 2B–2E. As an example, in FIG. 2B, a helically coiled polypeptide structure 16 comprises a protein A fragment (FB) linked to the amino terminal end of a $V_H$-like domain 10 via a spacer 18. FIG. 2C illustrates a bifunctional protein having an effector polypeptide 20 linked via spacer 22 to the carboxyl terminus of polypeptide 14 of binding protein segment 2. This effector polypeptide 20 may consist of, for example, a toxin, therapeutic drug, binding protein, enzyme or enzyme fragment, site of attachment for an imaging agent (e.g., to chelate a radioactive ion such as indium), or site of selective attachment to an immobilization matrix so that the BABS can be used in affinity chromatography or solid phase binding assay. This effector alternatively may be linked to the amino terminus of polypeptide 10, although trailers are preferred. FIG. 2D depicts a trifunctional protein comprising a linked pair of BABS 2 having another distinct protein domain 20 attached to the N-terminus of the first binding protein segment. Use of multiple BABS in a single protein enables production of constructs having very high selective affinity for multiepitopic sites such as cell surface proteins.

The independently functional domains are attached by a spacer 18 (FIGS. 2B and 2D) covalently linking the C terminus of the protein 16 or 20 to the N-terminus of the first domain 10 of the binding protein segment 2, or by a spacer 22 linking the C-terminus of the second binding domain 14 to the N-terminus of another protein (FIGS. 2C and 2D). The spacer may be an amino acid sequence analogous to linker sequence 12, or it may take other forms. As noted above, the spacer's primary function is to separate the active protein regions to promote their independent bioactivity and permit each region to assume its bioactive conformation independent of interference from its neighboring structure.

Figure 2E:
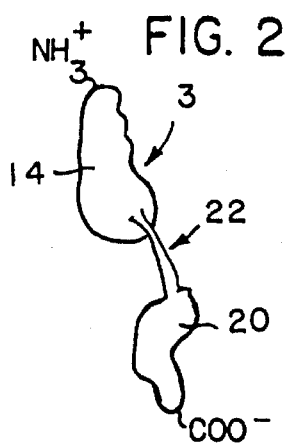

FIG. 2E depicts another type of reagent, comprising a BABS having only one set of three CDRs, e.g., analogous to a heavy chain variable region, which retains a measure of affinity for the antigen. Attached to the carboxyl end of the polypeptide 10 or 14 comprising the FR and CDR sequences constituting the binding site 3 through spacer 22 is effector polypeptide 20 as described above.

As is evidenced from the foregoing, the invention provides a large family of reagents comprising proteins, at least a portion of which defines a binding site patterned after the variable region of an immunoglobulin. It will be apparent that the nature of any protein fragments linked to the BABS, and used for reagents embodying the invention, are essentially unlimited, the essence of the invention being the provision, either alone or linked to other proteins, of binding sites having specificities to any antigen desired.

The clinical administration of multifunctional proteins comprising a BABS, or a BABS alone, affords a number of advantages over the use of intact natural or chimeric antibody molecules, fragments thereof, and conjugates comprising such antibodies linked chemically to a second bioactive moiety. The multifunctional proteins described herein offer fewer cleavage sites to circulating proteolytic enzymes, their functional domains are connected by peptide bonds to polypeptide linker or spacer sequences, and thus the proteins have improved stability. Because of their smaller size and efficient design, the multifunctional proteins described herein reach their target tissue more rapidly, and are cleared more quickly from the body. They also have reduced immunogenicity. In addition, their design facilitates coupling to other moieties in drug targeting and imaging application. Such coupling may be conducted chemically after expression of the BABS to a site of attachment for the coupling product engineered into the protein at the DNA level. Active effector proteins having toxic, enzymatic, binding, modulating, cell differentiating, hormonal, or other bioactivity are expressed from a single DNA as a leader and/or trailer sequence, peptide bonded to the BABS.

Design and Manufacture

The proteins of the invention are designed at the DNA level. The chimetic or synthetic DNAs are then expressed in a suitable host system, and the expressed proteins are collected and renatured if necessary. A preferred general structure of the DNA encoding the proteins is set forth in FIG. 8. As illustrated, it encodes an optimal leader sequence used to promote expression in procaryotes having a built-in cleavage site recognizable by a site specific cleavage agent, for example, an endopeptidase, used to remove the leader after expression. This is followed by DNA encoding a $V_H$-like domain, comprising CDRs and FRs, a linker, a $V_L$-like domain, again comprising CDRs and FRs, a spacer, and an effector protein. After expression, folding, and cleavage of the leader, a bifunctional protein is produced having a binding region whose specificity is determined by the CDRs, and a peptide-linked independently functional effector region.

The ability to design the BABS of the invention depends on the ability to determine the sequence of the amino acids in the variable region of monoclonal antibodies of interest, or the DNA encoding them. Hybridoma technology enables production of cell lines secreting antibody to essentially any desired substance that produces an immune response. RNA encoding the light and heavy chains of the immunoglobulin can then be obtained from the cytoplasm of the hybridoma. The 5end portion of the mRNA can be used to prepare cDNA for subsequent sequencing, or the amino acid sequence of the hypervariable and flanking framework regions can be determined by amino acid sequencing of the V region fragments of the H and L chains. Such sequence analysis is now conducted routinely. This knowledge, coupled with observations and deductions of the generalized structure of immunoglobulin Fvs, permits one to design synthetic genes encoding FR and CDR sequences which likely will bind the antigen. These synthetic genes are then prepared using known techniques, or using the technique disclosed below, inserted into a suitable host, and expressed, and the expressed protein is purified. Depending on the host cell, renaturation techniques may be required to attain proper conformation. The various proteins are then tested for binding ability, and one having appropriate affinity is selected for incorporation into a reagent of the type described above. If necessary, point substitutions seeking to optimize binding may be made in the DNA using conventional casette mutagenesis or other protein engineering methodology such as is disclosed below.

Preparation of the proteins of the invention also is dependent on knowledge of the amino acid sequence (or corresponding DNA or RNA sequence) of bioactive proteins such as enzymes, toxins, growth factors, cell differentiation factors, receptors, anti-metabolites, hormones or various cytokines or lymphokines. Such sequences are reported in the literature and available through computerized data banks.

The DNA sequences of the binding site and the second protein domain are fused using conventional techniques, or assembled from synthesized oligonucleotides, and then expressed using equally conventional techniques.

The processes for manipulating, amplifying, and recombining DNA which encode amino acid sequences of interest are generally well known in the art, and therefore, not described in detail herein. Methods of identifying and isolating genes encoding antibodies of interest are well understood, and described in the patent and other literature. In general, the methods involve selecting genetic material coding for amino acids which define the proteins of interest, including the CDRs and FRs of interest, according to the genetic code.

Accordingly, the construction Of DNAs encoding proteins as disclosed herein can be done using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, and synthetic probes for isolating immunoglobulin or other bioactive protein genes. Various promoter sequences and other regulatory DNA sequences used in achieving expression, and various types of host cells are also known and available. Conventional transfect ion techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

One method for obtaining DNA encoding the proteins disclosed herein is by assembly of synthetic oligonucleotides produced in a conventional, automated, polynucleotide synthesizer followed by ligation with appropriate ligases. For example, overlapping, complementary DNA fragments comprising 15 bases may be synthesized semi manually using phosphoramidite chemistry, with end segments left unphosphorylated to prevent polymerization during ligation. One end of the synthetic DNA is left with a "sticky end" corresponding to the site of action-of a particular restriction endonuclease, and the other end is left with an end corresponding to the site of action of another restriction endonuclease. Alternatively, this approach can be fully automated. The DNA encoding the protein may be created by synthesizing longer single strand fragments (e.g., 50-100 nucleotides long) in, for example, a Biosearch oligonucleotide synthesizer, and then ligating the fragments.

A method of producing the BABS of the invention is to produce a synthetic DNA encoding a polypeptide comprising, e.g., human FRs, and intervening "dummy" CDRs, or amino acids having no function except to define suitably situated unique restriction sites. This synthetic DNA is then altered by DNA replacement, in which restriction and ligation is employed to insert synthetic oligonucleotides encoding CDRs defining a desired binding specificity in the proper location between the FRs. This approach facilitates empirical refinement of the binding properties of the BABS.

This technique is dependent upon the ability to cleave a DNA corresponding in structure to a variable domain gene at specific sites flanking nucleotide sequences encoding CDRs. These restriction sites in some cases may be found in the native gene. Alternatively, non-native restriction sites may be engineered into the nucleotide sequence resulting in a synthetic gene with a different sequence of nucleotides than the native gene, but encoding the same variable region amino acids because of the degeneracy of the genetic code. The fragments resulting from endonuclease digestion, and comprising FR-encoding sequences, are then ligated to non-native CDR-encoding sequences to produce a synthetic variable domain gene with altered antigen binding specificity. Additional nucleotide sequences encoding, for example, constant region amino acids or a bioactive molecule may then be linked to the gene sequences to produce a bifunctional protein.

The expression of these synthetic DNA's can be achieved in both prokaryotic and eucaryotic systems via transfection with an appropriate vector. In *E. coli* and other microbial hosts, the synthetic genes can be expressed as fusion protein which is subsequently cleaved. Expression in eucaryotes can be accomplished by the transfection of DNA sequences encoding CDR and FR region amino acids and the amino acids defining a second function into a myeloma or other type of cell line. By this strategy intact hybrid antibody molecules having hybrid Fv regions and various bioactive proteins including a biosynthetic binding site may be produced. For fusion protein expressed in bacteria, subsequent proteolytic cleavage of the isolated fusions can be performed to yield free BABS, which can be renatured to obtain an intact biosynthetic, hybrid antibody binding site.

Heretofore, it has not been possible to cleave the heavy and light chain region to separate the variable and constant regions of an immunoglobulin so as to produce intact Fv, except in specific cases not of commercial utility. However, one method of producing BABS in accordance with this invention is to redesign DNAs encoding the heavy and light chains of an immunoglobulin, optionally altering its specificity or humanizing its FRs, and incorporating a cleavage site and "hinge region" between the variable and constant regions of both the heavy and light chains. Such chimetic antibodies can be produced in transfectomas or the like and subsequently cleaved using a preselected endopeptidase.

The hinge region is a sequence of amino acids which serve to promote efficient cleavage by a preselected cleavage agent at a preselected, built-in cleavage site. It is designed to promote cleavage preferentially at the cleavage site when the polypeptide is treated with the cleavage agent in an appropriate environment.

The hinge region can take many different forms. Its design involves selection of amino acid residues (and a DNA fragment encoding them) which impart to the region of the fused protein about the cleavage site an appropriate polarity, charge distribution, and stereochemistry which, in the aqueous environment where the cleavage takes place, efficiently exposes the cleavage site to the cleavage agent in preference to other potential cleavage sites that may be present in the polypeptide, and/or to improve the kinetics of the cleavage reaction. In specific cases, the amino acids of the hinge are selected and assembled in sequence based on their known properties, and then the fused polypeptide sequence is expressed, tested, and altered for refinement.

The hinge region is free of cysteine. This enables the cleavage reaction to be conducted under conditions in which the protein assumes its tertiary conformation, and may be held in this conformation by intramolecular disulfide bonds. It has been discovered that in these conditions access of the protease to potential cleavage sites which may be present within the target protein is hindered. The hinge region may comprise an amino acid sequence which includes one or more proline residues. This allows formation of a substantially unfolded molecular segment. Aspattic acid, glutamic acid, arginine, lysine, serine, and threonine residues maximize ionic interactions and may be present in amounts and/or in sequence which renders the moiety comprising the hinge water soluble.

The cleavage site preferably is immediately adjacent the Fv polypeptide chains and comprises one amino acid or a sequence of amino acids exclusive of any sequence found in the amino acid structure of the chains in the Fv. The cleavage site preferably is designed for unique or preferential cleavage by a specific selected agent. Endopeptidases are preferred, although non-enzymatic (chemical) cleavage agents may be used. Many useful cleavage agents, for instance, cyanogen bromide, dilute acid, trypsin, *Staphylococcus aureus* V-8 protease, post proline cleaving enzyme, blood coagulation Factor Xa, enterokinase, and renin, recognize and preferentially or exclusively cleave particular cleavage sites. One currently preferred cleavage agent is V-8 protease. The currently preferred cleavage site is a Glu residue. Other useful enzymes recognize multiple residues as a cleavage site, e.g., factor Xa (Ile-Glu-Gly-Arg) or enterokinase (Asp-Asp-Asp-Asp-Lys). The principles of this selective cleavage approach may also be used in the design of the linker and spacer sequences of the multifunctional constructs of the invention where an exciseable linker or selectively cleavable linker or spacer is desired.

Design of Synthetic $V_H$ and $V_L$ Mimics

FRs from the heavy and light chain murine anti-digoxin monoclonal 26-10 (FIGS. 4A and 4B) were encoded on the same DNAs with CDRs from the murine anti-lysozyme monoclonal glp-4 heavy chain (FIG. 3 sequence 1) and light chain to produce $V_H$ (FIG. 4C) and $V_L$ (FIG. 4D) regions together defining a biosynthetic antibody binding site which is specific for lysozyme. Murine CDRs from both the heavy and light chains of monoclonal glp-4 were encoded on the same DNAs with FRs from the heavy and light chains of human myeloma antibody NEWM (FIGS. 4E and 4F). The resulting interspecies chimetic antibody binding domain has reduced immunogenicity in humans because of its human FRs, and specificity for lysozyme because of its murine CDRs.

A synthetic DNA was designed to facilitate CDR insertions into a human heavy chain FR and to facilitate empirical refinement of the resulting chimetic amino acid sequence. This DNA is depicted in FIG. 5.

A synthetic, bifunctional FB-binding site protein was also designed at the DNA level, expressed, purified, renatured, and shown to bind specifically with a preselected antigen (digoxin) and Fc. The detailed primary structure of this construct is shown in FIG. 6; its tertiary structure is illustrated schematically in FIG. 2B.

Details of these and other experiments, and additional design principles on which the invention is based, are set forth below.

GENE DESIGN AND EXPRESSION

Given known variable region DNA sequences, synthetic $V_L$ and $V_H$ genes may be designed which encode native or near native FR and CDR amino acid sequences from an antibody molecule, each separated by unique restriction sites located as close to FR-CDR and CDR-FR borders as possible. Alternatively, genes may be designed which encode native FR sequences which are similar or identical to the FRs of an antibody molecule from a selected species, each separated by "dummy" CDR sequences containing strategically located restriction sites. These DNAs serve as starting materials for producing BABS, as the native or "dummy" CDR sequences may be excised and replaced with sequences encoding the CDR amino acids defining a selected binding site. Alternatively, one may design and directly synthesize native or near-native FR sequences from a first antibody molecule, and CDR sequences from a second antibody molecule. Any one of the $V_H$ and $V_L$ sequences described above may be linked together directly, via an amino acids chain or linker connecting the C-terminus of one chain with the N-terminus of the other.

These genes, once synthesized, may be cloned with or without additional DNA sequences coding for, e.g., an antibody constant region, enzyme, or toxin, or a leader peptide which facilitates secretion or intracellular stability of a fusion polypeptide. The genes then can be expressed directly in an appropriate host cell, or can be further engineered before expression by the exchange of FR, CDR, or "dummy" CDR sequences with new sequences. This manipulation is facilitated by the presence of the restriction sites which have been engineered into the gene at the FR-CDR and CDR-FR borders.

FIG. 3 illustrates the general approach to designing a chimeric $V_H$; further details of exemplary designs at the DNA level are shown in FIGS. 4A–4F. FIG. 3, lines 1 and 2, show the amino acid sequences of the heavy chain variable region of the murine monoclonals glp-4 (anti-lysozyme) and 26-10 (anti-digoxin), including the four FR and three CDR sequences of each. Line 3 shows the sequence of a chimeric $V_H$ which comprises 26-10 FRs and glp-4 CDRs. As illustrated, the hybrid protein of line 3 is identical to the native protein of line 2, except that 1) the sequence TFTNYYIHWLK has replaced the sequence IFTDF YM NW VR, 2) EWIGWIYPGNGNTKYNENFKG has replaced DYIGYISPYSGVTGYNQKFKG, 3) RYTHYYF has replaced GSSGNKWAM, and 4) A has replaced V as the sixth amino acid beyond CDR-2. These changes have the effect of changing the specificity of the 26-10 $V_H$ to mimic the specificity of glp-4. The Ala to Val single amino acid replacement within the relatively conserved framework region of 26-10 is an example of the replacement of an amino acid outside the hypervariable region made for the purpose of altering specificity by CDR replacement. Beneath sequence 3 of FIG. 3, the restriction sites in the DNA encoding the chimeric $V_H$ (see FIGS. 4A–4F) are shown which are disposed about the CDR-FR borders.

Lines 4 and 5 of FIG. 3 represent another construct. Line 4 is the full length $V_H$ of the human antibody NEWM. That human antibody may be made specific for lysozyme by CDR replacement as shown in line 5. Thus, for example, the segment TFTNYYIHWLK from glp-4 replaces TFSNDYYTWVR of NEWM, and its other CDRs are replaced as shown. This results in a $V_H$ comprising a human framework with murine sequences determining specificity.

By sequencing any antibody, or obtaining the sequence from the literature, in view of this disclosure one skilled in the art can produce a BABS of any desired specificity comprising any desired framework region. Diagrams such as FIG. 3 comparing the amino acid sequence are valuable in suggesting which particular amino acids should be replaced to determine the desired complementarity. Expressed sequences may be tested for binding and refined by exchanging selected amino acids in relatively conserved regions, based on observation of trends in amino acid sequence data and/or computer modeling techniques.

Significant flexibility in $V_H$ and $V_L$ design is possible because the amino acid sequences are determined at the DNA level, and the manipulation of DNA can be accomplished easily.

For example, the DNA sequence for murine $V_H$ and $V_L$ 26-10 containing specific restriction sites flanking each of the three CDRs was designed with the aid of a commercially available computer program which performs combined reverse translation and restriction site searches ("RV.exe" by Compugene, Inc.). The known amino acid sequences for $V_H$ and $V_L$ 26-10 polypeptides were entered, and all potential DNA sequences which encode those peptides and all potential restriction sites were analyzed by the program. The program can, in addition, select DNA sequences encoding the peptide using only codons preferred by E. coli if this bacterium is to be host expression organism of choice. FIGS. 4A and 4B show an example of program output. The nuelic acid sequences of the synthetic gene and the corresponding amino acids are shown. Sites of restriction andenuclease cleavage are also indicated. The CDRs of these synthetic genes are underlined.

The DNA sequences for the synthetic 26-10 $V_H$ and $V_L$ are designed so that one or both of the restriction sites flanking each of the three CDRs are unique. A six base site (such as that recognized by Bsm I or BspM I) is preferred, but where six base sites are not possible, four or five base sites are used. These sites, if not already unique, are rendered unique within the gene by eliminating other occurrences within the gene without altering necessary amino acid sequences. Preferred cleavage sites are those that, once cleaved, yield fragments with sticky ends just outside of the boundary of the CDR within the framework. However, such ideal sites are only occasionally possible because the FR-CDR boundary is not an absolute one, and because the amino acid sequence of the FR may not permit a restriction site. In these cases, flanking sites in the FR which are more distant from the predicted boundary are selected.

FIG. 5 discloses the nucleotide and corresponding amino acid sequence (shown in standard single letter code) of a synthetic DNA comprising a master framework gene having the generic structure:

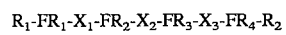

where $R_1$ and $R_2$ are restricted ends which are to be ligated into a vector, and $X_1$, $X_2$, and $X_3$ are DNA sequences whose function is to provide convenient restriction sites for CDR insertion. This particular DNA has murine FR sequences and unique, 6-base restriction sites adjacent the FR borders so that nucleotide sequences encoding CDRs from a desired monoclonal can be inserted easily. Restriction endonuclease digestion sites are indicated with their abbreviations; enzymes of choice for CDR replacement are underscored. Digestion of the gene with the following restriction endonucleases results in 3' and 5' ends which can easily be matched up with and ligated to native or synthetic CDRs of desired specificity; KpnI and BstXI are used for ligation of $CDR_1$; XbaI and DraI for $CDR_2$; and BssHII and ClaI for $CDR_3$.

OLIGONUCLEOTIDE SYNTHESIS

The synthetic genes and DNA fragments designed as described above preferably are produced by assembly of chemically synthesized oligonucleotides. 15-100met oligonucleotides may be synthesized on a Biosearch DNA Model 8600 Synthesizer, and purified by polyacrylamide gel electrophoresis (PAGE) in Tris-Borate-EDTA buffer (TBE). The DNA is then electroeluted from the gel. Overlapping oligomers may be phosphorylated by T4 polynucleotide kinase and ligated into larger blocks which may also be purified by PAGE.

CLONING OF SYNTHETIC OLIGONUCLEOTIDES

The blocks or the pairs of longer oligonucleotides may be cloned into E. coli using a suitable, e.g., pUC, cloning vector. Initially, this vector may be altered by single strand mutagenesis to eliminate residual six base altered sites. For example, $V_H$ may be synthesized and cloned into pUC as five primary blocks spanning the following restriction sites: 1. EcoRI to first NarI site; 2. first NarI to XbaI; 3. XbaI to SalI; 4. SalI to NcoI; 5. NcoI to Bam HI. These cloned fragments may then be isolated and assembled in several three-fragment ligations and cloning steps into the pUC8 plasmid. Desired ligations selected by PAGE are then transformed into, for example, *E. coli* strain JM83, and plated onto LB Ampicillin +Xgal plates according to standard procedures. The gene sequence may be confirmed by supercoil sequencing after cloning, or after subcloning into M13 via the dideoxy method of Sanger.

PRINCIPLE OF CDR EXCHANGE

Three CDRs (or alternatively, four FRs) can be replaced per $V_H$ or $V_L$. In simple cases, this can be accomplished by cutting the shuttle pUC plasmid containing the respective genes at the two unique restriction sites flanking each CDR or FR, removing the excised sequence, and ligating the vector with a native nucleic acid sequence or a synthetic oligonucleotide encoding the desired CDR or FR. This three part procedure would have to be repeated three times for total CDR Ieplacement and four times for total FR replacement. Alternatively, a synthetic nucleotide encoding two consecutive CDRs separated by the appropriate FR can be ligated to a pUC or other plasmid containing a gene whose corresponding CDRs and FR have been cleaved out. This procedure reduces the number of steps required to perform CDR and/or FR exchange.

EXPRESS OF PROTEINS

The engineered genes can be expressed in appropriate prokaryotic hosts such as various strains of *E. coil*, and in eucaryotic hosts such as Chinese hamster ovary cell, murine myeloma, and human myeloma/transfectoma cells.

For example, if the gene is to be expressed in *E. coil*, it may first be cloned into an expression vector. This is accomplished by positioning the engineered gene downstream from a promoter sequence such as trp or tac, and a gene coding for a leader peptide. The resulting expressed fusion protein accumulates in refractlie bodies in the cytoplasm of the cells, and may be harvested after disruption of the cells by French press or sonication. The refractlie bodies are solubilized, and the expressed proteins refolded and cleaved by the methods already established for many other recombinant proteins.

If the engineered gene is to be expressed in myeloma cells, the conventional expression system for immunoglobulins, it is first inserted into an expression vector containing, for example, the Ig promoter, a secretion signal, immunoglobulin enhancers, and various introns. This plasmid may also contain sequences encoding all or part of a constant region, enabling an entire part of a heavy or light chain to be expressed. The gene is transfected into myeloma cells via established electroporation or protoplast fusion methods. Cells so transfected can express $V_L$ or $V_H$ fragments, $V_{L2}$ or $V_{H2}$ homodimers, $V_L$-$V_H$ heterodimers, $V_H$-$V_L$ or $V_L$-$V_H$ single chain polypeptides, complete heavy or light immunoglobulin chains, or portions thereof, each of which may be attached in the various ways discussed above to a protein region having another function (e.g., cytoto xicity).

Vectors containing a heavy chain V region (or V and C regions) can be contransfected with analogous vectors carrying a light chain V region (or V and C regions), allowing for the expression of noncovalently associated binding sites (or complete antibody molecules).

In the examples which follow, a specific example of how to make a single chain binding site is disclosed, together with methods employed to assess its binding properties. Thereafter, a protein construct having two functional domains is disclosed. Lastly, there is disclosed a series of additional targeted proteins which exemplify the invention.
Example Of CDR Exchange and Expression The synthetic gene coding for murine $V_H$ and $V_L$ 26-10 shown in FIGS. 4A and 4B were designed from the known amino acid sequence of the protein with the aid of Compugene, a software program. These genes, although coding for the native amino acid sequences, also contain non-native and often unique restriction sites flanking nucleic acid sequences encoding CDR's to facilitate CDR replacement as noted above.

Both the 3' and 5' ends of the large synthetic oligomers were designed to include 6-base restriction sites, present in the genes and the pUC vector. Furthermore, those restriction sites in the synthetic genes which were only suited for assembly but not for cloning the pUC were extended by "helper" cloning sites with matching sites in pUC.

Cloning of the synthetic DNA and later assembly of the gene is facilitated by the spacing of unique restriction sites along the gene. This allows corrections and modifications by cassette mutagenesis at any location. Among them are alterations near the 5' or 3' ends of the gene as needed for the adaptation to different expression vectors. For example, a PstI site is positioned near the 5' end of the $V_H$ gene. Synthetic linkers can be attached easily between this site and a restriction site in the expression plasmid. These genes were synthesized by assembling oligonucleotides as described above using a Biosearch Model 8600 DNA Synthesizer. They were ligated to vector pUC8 for transformation of *E. coli*.

Specific CDRs may be cleaved from the synthetic $V_H$ gene by digestion with the following pairs of restriction endonucleases: HpHI and BstXI for $CDR_1$; XbaI and DraI for $CDR_2$; and BanII and BanI for $CDR_3$. After removal on one CDR, another CDR of desired specificity may be ligated directly into the restricted gene, in its place if the 3' and 5' ends of the restricted gene and the new CDR contain complementary single stranded DNA sequences.

In the present example, the three CDRs of each of murine $V_H$ 26-10 and $V_L$ 26-10 were replaced with the corresponding CDRs of glp-4. The nucleic acid sequences and corresponding amino acid sequences of the chimeric $V_H$ and $V_L$ genes encoding the FRs of 26-10 and CDRs of glp-4 are shown in FIGS. 4C and 4D. The positions of the restriction endonuclease cleavage sites are noted with their standard abbreviations. CDR sequences are underlined as are the restriction endonucleases of choice useful for further CDR replacement.

These genes were cloned into pUC8, a shuttle plasmid. To retain unique restriction sites after cloning, the $V_H$-like gene was spliced into the EcoR1 and HindIII or BamHI sites of the plasmid.

Direct expression of the genes may be achieved in *E. coli*. Alternatively, the gene may be preceded by a leader sequence and expressed in *E. coli* as a fusion product by splicing the fusion gene into the host gene whose expression is regulated by interaction of a repressor with the respective operator. The protein can be induced by starvation in minimal medium and by chemical inducers. The $V_H$-$V_L$ biosynthetic 26-10 gene has been expressed as such a fusion protein behind the trp and tac promoters. The gene translation product of interest may then be cleaved from the leader in the fusion protein by e.g., cyanogen bromide degradation, tryptic digestion, mild acid cleavage, and/or digestion with factor Xa protease. Therefore, a shuttle plasmid containing a synthetic gene encoding a leader peptide having a site for mild acid cleavage, and into which has been spliced the synthetic BABS gene was used for this purpose. In addition, synthetic DNA sequences encoding a signal peptide for secretion of the processed target protein into the periplasm of the host cell can also be incorporated into the plasmid.

After harvesting the gene product and optionally releasing it from a fusion peptide, its activity as an antibody binding site and its specificity for glp-4 (lysozyme) epitope are assayed by established immunological techniques, e.g., affinity chromatography and radioimmunoassay. Correct folding of the protein to yield the proper three-dimensional conformation of the antibody binding site is prerequisite for its activity. This occurs spontaneously in a host such as a myeloma cell which naturally expresses immunoglobulin proteins. Alternatively, for bacterial expression, the protein forms inclusion bodies which, after harvesting, must be subjected to a specific sequence of solvent conditions (e.g., diluted 20×from 8M urea 0.1M Tris-HCl pH 9 into 0.15M NaCl, 0.01M sodium phosphate, pH 7.4 (Hochman et al. (1976) Biochem. 15:2706–2710) to assume its correct conformation and hence its active form.

FIGS. 4E and 4F show the DNA and amino acid sequence of chimeric $V_H$ and $V_L$ comprising human FRs from NEWM and murine CDRs from glp-4. The CDRS are underlined, as are restriction sites of choice for further CDR replacement or empirically determined refinement.

These constructs also constitute master framework genes, this time constructed of human framework sequences. They may be used to construct BABS of any desired specificity by appropriate CDR replacement.

Binding sites with other specificities have also been designed using the methodologies disclosed herein. Examples include those having FRs from the human NEWM antibody and CDRs from murine 26-10 (FIG. 9A), murine 26-10 FRs and G-loop CDRs (FIG. 9B), FRs and CDRs from murine MOPC-315 (FIG. 9C), FRs and CDRs from an anti-human carcinoembryonic antigen monoclonal antibody (FIG. 9D), and FRs and CDRs 1, 2, and 3 from $V_L$ and FRs and CDR 1 and 3 from the $V_H$ of the anti-CEA antibody, with CDR 2 from a consensus immunoglobulin gene (FIG. 9E).

II. Model Binding Site:

The digoxin binding site of the $IgG_{2a,k}$ monoclonal antibody 26-10 has been analyzed by Mudgett-Hunter and colleagues (unpublished). The 26-10 V region sequences were determined from both amino acid sequencing and DNA sequencing of 26-10 H and L chain mRNA transcripts (D. Panka, J. N. & M. N. M., unpublished data). The 26-10 antibody exhibits a high digoxin binding affinity [$K_o$=5.4 ×10$^9$ M$^{-1}$] and has a well-defined specificity profile, providing a baseline for comparison with the biosynthetic binding sites mimicking its structure.

Protein Design:

Crystallographically determined atomic coordinates for Fab fragments of 26-10 were obtained from the Brookhaven Data Bank. Inspection of the available three-dimensional structures of Fv regions within their parent Fab fragments indicated that the Euclidean distance between the C-terminus of the $V_H$ domain and the N-terminus of the $V_L$ domain is about 35 Å. Considering that the peptide unit length is approximately 3.8 Å, a 15 residue linker was selected to bridge this gap. The linker was designed so as to exhibit little propensity for secondary structure and not to interfere with domain folding. Thus, the 15 residue sequence (Gly-Gly-Gly-Gly-Ser)$_3$ was selected to connect the $V_H$ carboxyl- and $V_L$ amino-termini.

Binding studies with single chain binding sites having less than or greater than 15 residues demonstrate the importance of the prerequisite distance which must separate $V_H$ from $V_L$; for example, a (Gly$_4$-Ser)$_1$ linker does not demonstrate binding activity, and those with (Gly$_4$-Ser)$_5$ linkers exhibit very low activity compared to those with (Gly$_4$-Ser)$_3$ linkers.

Gene Synthesis:

Design of the 744 base sequence for the synthetic binding site gene was derived from the Fv protein sequence of 26-10 by choosing codons frequently used in *E. coli*. The model of this representative synthetic gene is shown in FIG. 8, discussed previously. Synthetic genes coding for the trp Promoter-operator, the modified trp LE leader peptide (MLE), the sequence of which is shown in FIG. 10A, and $V_H$ were prepared largely as described previously. The gene coding for $V_H$ was assembled from 46 chemically synthesized oligonucleotides, all 15 bases long, except for terminal fragments (13 to 19 bases) that included cohesive cloning ends. Between 8 and 15 overlapping oligonucleotides were enzymatically ligated into double stranded DNA, cut at restriction sites suitable for cloning (NarI, XbaI, SalI, SacII, SacI), purified by PAGE on 8% gels, and cloned in pUC which was modified to contain additional cloning sites in the polylinker. The cloned segments were assembled stepwise into the complete gene mimicking $V_H$ by ligations in the pUC cloning vector.

The gene mimicking 26-10 $V_L$ was assembled from 12 long synthetic polynucleotides ranging in size from 33 to 88 base pairs, prepared in automated DNA synthesizers (Model 6500, Biosearch, San Rafael, Calif.; Model 380A, Applied Biosystems, Foster City, Calif.). Five individual double stranded segments were made out of pairs of long synthetic oligonucleotides spanning six-base restriction sites in the gene (AatII, BstEII, PpnI, HindIII, BglII, and PstI). In one case, four long overlapping strands were combined and cloned. Gene fragments bounded by restriction sites for assembly that were absent from the pUC polylinker, such as AatII and BstEII, were flanked by EcoRI and BamHI ends to facilitate cloning.

The linker between $V_H$ and $V_L$, encoding (Gly-Gly-Gly-Gly-Ser)$_3$, was cloned from two long synthetic oligonucleotides, 54 and 62 bases long, spanning SacI and AatII sites, the latter followed by an EcoRI cloning end. The complete single chain binding site gene was assembled from the $V_H$, $V_L$, and linker genes to produce a construct, corresponding to aspartyl-prolyl-$V_H$-<linker>-$V_L$, flanked by EcoRI and PstI restriction sites.

The trp promoter-operator, starting from its SspI site, was assembled from 12 overlapping 15 base oligomers, and the MLE leader gene was assembled from 24 overlapping 15 base oligomers. These were cloned and assembled in pUC using the strategy of assembly sites flanked by cloning sites. The final expression plasmid was constructed in the pBR322 vector by a 3-part ligation using the sites SspI, EcoRI, and PstI (see FIG. 10B). Intermediate DNA fragments and assembled genes were sequenced by the dideoxy method.

Fusion Protein Expression:

Single-chain protein was expressed as a fusion protein. The MLE leader gene (FIG. 10A) was derived from *E. coli* trp LE sequence and expressed under the control of a synthetic trp promoter and operator. *E. coli* strain JM83 was transformed with the expression plasmid and protein expression was induced in M9 minimal medium by addition of indoleacrylic acid (10 μg/ml) at a cell density with $A_{600}$=1. The high expression levels of the fusion protein resulted in its accumulation as insoluble protein granules, which were harvested from cell paste (FIG. 11, Lane 1).

Fusion Protein Cleavage:

The MLE leader was removed from the binding site protein by acid cleavage of the Asp-Pro peptide bond engineered at the junction of the MLE and binding site sequences. The washed protein granules containing the fusion protein were cleaved in 6M guanidine-HC1+10% acetic acid, pH 2.5, incubated at 37° C. for 96 hrs. The reaction was stopped through precipitation by addition of a 10-fold excess of ethanol with overnight incubation at −20° C., followed by centrifugation and storage at −20° C. until further purification (FIG. 11, Lane 2).

Protein Purification:

The acid cleaved binding site was separated from remaining intact fused protein species by chromatography on DEAE cellulose. The precipitate obtained from the cleavage mixture was redissolved in 6M guanidine-HCl+0.2M Tris-HCl, pH 8.2,+0.1M 2-mercaptoethanol and dialyzed exhaustively against 6 M urea+2.5 mMTris-HCl, pH 7.5,+1 mM EDTA. 2-Mercaptoethanol was added to a final concentration of 0.1M, the solution was incubated for 2 hrs at room temperature and loaded onto a 2.5×45 cm column of DEAE cellulose (Whatman DE 52), equilibrated with 6M urea+2.5 mMTris-HCl+1 mM EDTA, pH 7.5. The intact fusion protein bound weakly to the DE 52 column such that its elution was retarded relative to that of the binding protein. The first protein fractions which eluted from the column after loading and washing with urea buffer contained BABS protein devoid of intact fusion protein. Later fractions contaminated with some fused protein were pooled, rechromatographed on DE 52, and recovered single chain binding protein combined with other purified protein into a single pool (FIG. 11, Lane 3).

Refolding:

The 26-10 binding site mimic was refolded as follows: the DE 52 pool, disposed in 6M urea+2.5 mM Tris-HCl+1 mM EDTA, was adjusted to pH 8 and reduced with 0.1 M 2-mercaptoethanol at 37° C. for 90 min. This was diluted at least 100-fold with 0.01M sodium acetate, pH 5.5, to a concentration below 10 µg/ml and dialyzed at 4° C. for 2 days against acetate buffer.

AFFINITY CHROMATOGRAPHY

Purification of active binding protein by affinity chromatography at 4° C. on a ouabain-amine-Sepharose column was performed. The dilute solution of refolded protein was loaded directly onto a pair of tandem columns, each containing 3 ml of resin equilibrated with the 0.01M acetate buffer, pH 5.5. The columns were washed individually with an excess of the acetate buffer, and then by sequential additions of 5 ml each of 1M NaCl, 20 mM ouabain, and 3M potassium thiocyanate dissolved in the acetate buffer, interspersed with acetate buffer washes. Since digoxin binding activity was still present in the eluate, the eluate was pooled and concentrated 20-fold by ultrafiltration (PM 10 membrane, 200 ml concentrator; Amicon), reapplied to the affinity columns, and eluted as described. Fractions with significant absorbance at 280 nm were pooled and dialyzed against PBSA or the above acetate buffer. The amounts of protein in the DE 52 and ouabain-Sepharose pools were quantitated by amino acid analysis following dialysis against 0.01M acetate buffer. The results are shown below in Table 1.

TABLE 1

Estimated Yields of BABS Protein During Purification

| Step | Wet wt. Per 1 | mg protein | Cleavage yield (%) prior step | Yield relative to fusion protein |
|---|---|---|---|---|
| Cell paste | 12.0 g | 1440.0 mg[a] | | |
| Fusion protein Granules | 2.3 g | 480.0 mg[a,b] | 100.0% | 100.0% |
| Acid Cleavage/ DE 52 pool | | 144.0 mg | 38.0[c] | 38.0[c] |
| Ouabain-Sepharose pool | | 18.1 mg | 12.6[d] | 4.7[e] |

[a]Determined by Lowry protein analysis
[b]Determined by absorbance measurements
[c]Determined by amino acid analysis
[d]Calculated from the amount of BABS protein specifically eluted from ouabain-Sepharose relative to that applied to the resin; values were determined by amino acid analysis
[e]Percentage yield calculated on a molar basis Sequence Analysis of Gene and Protein:

The complete gene was sequenced in both directions using the dideo xy method of Sanger which confirmed the gene was correctly assembled. The protein sequence was also verified by protein sequencing. Automated Edman degradation was conducted on intact protein (residues 1–40), as well as on two major CNBr fragments (residues 108–129 and 140–159) with a Model 470A gas phase sequencer equipped with a Model 120A on-line phenylthiohydantoin-amino acid analyzer (Applied Biosystems, Foster City, Calif.). Homogeneous binding protein fractionated by SDS-PAGE and eluted from gel strips with water, was treated with a 20,000-fold excess of CNBr, in 1% trifluoroacetic acid-acetonitrile (1:1), for 12 hrs at 25° (in the dark). The resulting fragments were separated by SDS-PAGE and transferred electrophoretically onto an Immobilon membrane (Millipore, Bedford, Mass.), from which stained bands were cut out and sequenced.

Specificity Determination:

specificities of anti-digoxin 26-10 Fab and the BABS were assessed by radioimmunoassay. Wells of microtiter plates were coated with affinity-purified goat anti-murine Fab fragment (ICN ImmunoBiologicals, Lisle, Ill.) at 10 µg/ml in PBSA overnight at 4° C. After the plates were washed and blocked with 1% horse serum in PBSA, solutions (50 µl) containing 26-10 Fab or the BABS in either PBSA or 0.01M sodium acetate at pH 5.5 were added to the wells and incubated 2–3 hrs at room temperature. After unbound antibody fragment was washed from the wells, 25 µl of a series of concentrations of cardiac glycosides ($10^{-4}$ to $10^{-11}$M in PBSA) were added. The cardiac glycosides tested included digoxin, digitoxin, digoxigenin, digitoxigenin, gitoxin, ouabain, and acetyl strophanthidin. After the addition of $^{125}$I-digo xin (25 µl, 50,000 cpm; Cambridge Diagnostics, Billerica, MA) to each well, the plates were incubated overnight at 4° C., washed and counted. The inhibition curves are plotted in FIG. 12. The relative affinities for each digoxin analogue were calculated by dividing the concentration of each analogue at 50% inhibition by the concentration of digo xin (or digoxigenin) that gave 50% inhibition. There is a displacement of inhibition curves for the BABS to lower glycoside concentrations than observed for 26-10 Fab, because less active BABS than 26-10 Fab was bound to the plate. When 0.25M urea was added to the BABS in 0.01M sodium acetate, pH 5.5, more active sFv was bound to the goat anti-murine Fab coating on the plate. This caused the BABS inhibition curves to shift toward higher glycoside concentrations, closer to the position of those for 26-10 Fab, although maintaining the relative positions of curves for sFv obtained in acetate buffer alone. The results, expressed as normalized concentration of inhibitor giving 50% inhibition of $^{125}$I-digoxin binding, are shown in Table 2.

TABLE 2

| 26-10 Antibody Species | Normalizing Glycoside | D | DG | DO | DOG | A-S | G | O |
|---|---|---|---|---|---|---|---|---|
| Fab | Digoxin | 1.0 | 1.2 | 0.9 | 1.0 | 1.3 | 9.6 | 15 |
|  | Digoxigenin | 0.9 | 1.0 | 0.8 | 0.9 | 1.1 | 8.1 | 13 |
| BABS | Digoxin | 1.0 | 7.3 | 2.0 | 2.6 | 5.9 | 62 | 150 |
|  | Digoxigenin | 0.1 | 1.0 | 0.3 | 0.4 | 0.8 | 8.5 | 21 |

D = Digoxin
DG = Digoxigenin
DO = Digitoxin
DOG = Digitoxigenin
A-S = Acetyl Strophanthidin
G = Gitoxin
O = Ouabain Affinity Determination:

Association constants were measured by equilibrium binding studies. In immunoprecipitation experiments, 100 μl of $^3$H-digoxin (New England Nuclear, Billerica, MA) at a series of concentrations ($10^{-7}$M to $10^{-11}$M) were added to 100 μl of 26-10 Fab or the BABS at a fixed concentration. After 2-3 hrs of incubation at room temperature, the protein was precipitated by the addition of 100 μl goat antiserum to murine Fab fragment (ICN Immuno-Biologicals), 50 μl of the IgG fraction of rabbit anti-goat IgG (ICN ImmunoBiologicals), and 50 μl of a 10% suspension of protein A-Sepharose (Sigma). Following 2 hrs at 4° C., bound and free antigen were separated by vacuum filtration on glass fiber filters (Vacuum Filtration Manifold, Millipore, Bedford, Mass.). Filter disks were then counted in 5 ml of association constants, $K_o$, were calculated from scintillation fluid with a Model 1500 Tri-Carb Liquid Scintillation Analyzer (Packard, Sterling, Va.). The Scatchard analyses of the untransformed radioligand binding data using LIGAND, a non-linear curve fitting program based on mass action. $K_o$s were also calculated by Sips plots and binding isotherms shown in FIG. 13A for the BABS and 13B for the Fab. For binding isotherms, data are plotted as the concentration of digoxin bound versus the log of the unbound digoxin concentration, and the dissociation constant is estimated from the ligand concentration at 50% saturation. These binding data are also plotted in linear form as Sips plots (inset), having the same abscissa as the binding isotherm but with the ordinate representing log r/(n–r), defined below. The average intrinsic association constant ($K_o$) was calculated from the modified Sips equation (39), log (r/n–r)=a log C–a log $K_o$, where r equals moles of digoxin bound per mole of antibody at an unbound digoxin concentration equal to C; n is the number of moles of digoxin bound at saturation of the antibody binding site, and a is an index of heterogeneity which describes the distribution of association constants about the average intrinsic association constant $K_o$. Least squares linear regression analysis of the data indicated correlation coefficients for the lines obtained were 0.96 for the BABS and 0.99 for 26-10 Fab. A summary of the calculated association constants are shown below in Table 3.

TABLE 3

| Method of Data Analysis | Association Constant, $K_o$ | |
|---|---|---|
|  | $K_o$ (BABS), M$^{-1}$ | $K_o$ (Fab), M$^{-1}$ |
| Scatchard plot | $(3.2 \pm 0.9) \times 10^7$ | $(1.9 \pm 0.2) \times 10^8$ |
| Sips plot | $2.6 \times 10^7$ | $1.8 \times 10^8$ |
| Binding isotherm | $5.2 \times 10^7$ | $3.3 \times 10^8$ |

III. Synthesis of a Multifunctional Protein

A nucleic acid sequence encoding the single chain binding site described above was fused with a sequence encoding the FB fragment of protein A as a leader to function as a second active region. As a spacer, the native amino acids comprising the last 11 amino acids of the FB fragment bonded to an Asp-Pro dilute acid cleavage site was employed. The FB binding domain of the FB consists of the immediately preceding 43 amino acids which assume a helical configuration (see FIG. 2B).

The gene fragments are synthesized using a Biosearch DNA Model 8600 Synthesizer as described above. Synthetic oligonucleotides are cloned according to established protocol described above using the pUC8 vector transfected into E. coli. The completed fused gene set forth in FIG. 6A is then expressed in E.coli.

After sonication, inclusion bodies were collected by centrifugation, and dissolved in 6M guanidine hydrochloride (GuHCl), 0.2M Tris, and 0.1M 2-mercaptoethanol (BME), pH 8.2. The protein was denatured and reduced in the solvent overnight at room temperature. Size exclusion chromatography was used to purify fusion protein from the inclusion bodies. A Sepharose 4B column (1.5×80 cm) was run in a solvent of 6M GuHCl and 0.01M NaOAc, pH 4.75. The protein solution was applied to the column at room temperature in 0.5–1.0 ml amounts. Fractions were collected and precipitated with cold ethanol. These were run on SDS gels, and fractions rich in the recombinant protein (approximately 34,000 D) were pooled. This offers a simple first step for cleaning up inclusion body preparations without suffering significant proteolytic degradation.

For refolding, the protein was dialyzed against 100 ml of the same GuHCl-Tris-BME solution, and dialysate was diluted 11-fold over two days to 0.55 M GuHCl, 0.01M Tris, and 0.01M BME. The dialysis sacks were then transferred to 0.01 M NaCl, and the protein was dialyzed exhaustively before being assayed by RIA's for binding of $^{125}$I-labelled digoxin. The refolding procedure can be simplified by making a rapid dilution with water to reduce the GuHCl concentration to 1.1M, and then dialyzing against phosphate buffered saline (0.15M NaCl, 0.05M potassium phosphate, pH 7, containing 0.03% MAN3), so that it is free of any GuHCl within 12 hours. Product of both types of preparation showed binding activity, as indicated in FIG. 7A.

Demonstration of Bifunctionality:

This protein with an FB leader and a fused BABS is bifunctional; the BABS can bind the antigen and the FB can bind the Fc regions of immunoglobulins. To demonstrate this dual and simulataneous activity several radioimmunoassays were performed.

Properties of the binding site were probed by a modification of an assay developed by Mudgett-Hunter et al. (J. Immunol. (1982) 129:1165–1172; Molec. Immunol. (1985) 22:477–488), so that it could be run on microtiter plates as a solid phase sandwich assay. Binding data were collected using goat anti-murine Fab antisera (gAmFab) as the primary antibody that initially coats the wells of the plate.

These are polyclonal antisera which recognize epitopes that appear to reside mostly on framework regions. The samples of interest are next added to the coated wells and incubated with the gAmFab, which binds species that exhibit appropriate antigenic sites. After washing away unbound protein, the wells are exposed to $^{125}$I-labelled (radioiodinated) digoxin conjugates, either as $^{125}$I-dig-BSA or $^{125}$I-dig-lysine.

The data are plotted in FIG. 7A, which shows the results of a dilution curve experiment in which the parent 26-10 antibody was included as a control. The sites were probed with $^{125}$I-dig-BSA as described above, with a series of dilutions prepared from initial stock solutions, including both the slowly refolded (1) and fast diluted/quickly refolded (2) single chain proteins. The parallelism between all three dilution curves indicates that gAmFab binding regions on the BABS molecule are essentially the same as on the Fv of authentic 26-10 antibody, i.e., the surface epitopes appear to be the same for both proteins.

The sensitivity of these assays is such that binding affinity of the Fv for digoxin must be at least $10^6$. Experimental data on digoxin binding yielded binding constants in the range of $10^8$ to $10^9 M^{-1}$. The parent 26-10 antibody has an affinity of $5.4 \times 10^9 M^{-1}$. Inhibition assays also indicate the binding of $^{125}$I-dig-lysine, and can be inhibited by unlabelled digoxin, digoxigenin, digitoxin, digitoxigenin, gitoxin, acetyl strophanthidin, and ouabain in a way largely parallel to the parent 26-10 Fab. This indicates that the specificity of the biosynthetic protein is substantially identical to the original monoclonal.

In a second type of assay, Digoxin-BSA is used to coat microtiter plates. Renatured BABS (FB-BABS) is added to the coated plates so that only molecules that have a competent binding site can stick to the plate. $^{125}$I-labelled rabbit IgG (radioligand) is mixed with bound FB-BABS on the plates. Bound radioactivity reflects the interation of IgG with the FB domain of the BABS, and the specificity of this binding is demonstrated by its inhibition with increasing amounts of FB, Protein A, rabbit IgG, IgG2a, and IgG1, as shown in FIG. 7B.

The following species were tested in order to demonstrate authentic binding: unlabelled rabbit IgG and IgG2a monoclona l antibody (which binds competiviely to the FB domain of the BABS); and protein A and FB (which bind competively to the radioligand). As shown in FIG. 7B, these species are found to completely inhibit radioligand binding, as expected. A monoclonal antibody of the IgG1 subclass binds poorly to the FB, as expected, inhibiting only about 34% of the radioligand from binding. These data indicate that the BABS domain and the FB domain have independent activity.

IV. OTHER CONSTRUCTS

Other BABS-containing protein constructed according to the invention expressible in *E. coli* and other host cells as described above are set forth in the drawing. These proteins may be bifunctional or multifunctional. Each construct includes a single chain BABS linked via a spacer sequence to an effector molecule comprising amino acids encoding a biologically active effector protein such as an enzyme, receptor, toxin, or growth factor. Some examples of such constructs shown in the drawing include proteins comprising epidermal growth factor (EGF) (FIG. 15A), streptavidin (FIG. 15B), tumor necrosis factor (TNF) (FIG. 15C), calmodulin (FIG. 5D) the beta chain of platelet derived growth factor (B-PDGF) (15E) ricin A (15F), interleukin 2 (15G) and FB dimer (15H). Each is used as a trailer and is connected to a preselected BABS via a spacer (Gly-Ser-Gly) encoded by DNA defining a Bam HI restriction site. Additional amino acids may be added to the spacer for empirical refinement of the construct if necessary by opening up the Bam HI site and inserting an oligonucleotide of a desired length having BamHI sticky ends. Each gene also terminates with a PstI site to facilitate insertion into a suitable expression vector.

The BABS of the EGF and PDGF constructs may be, for example, specific for fibrin so that the EGF or PDGF is delivered to the site of a wound. The BABS for TNF and ricin A may be specific to a tumor antigen, e.g., CEA, to produce a construct useful in cancer therapy. The calmodulin construct binds radioactive ions and other metal ions. Its BABS may be specific, for example, to fibrin or a tumor antigen, so that it can be used as an imaging agent to locate a thrombus or tumor. The streptavadin construct binds with biotin with very high affinity. The biotin may be labeled with a remotely detectable ion for imaging purposes. Alternatively, the biotin may be immobilized on an affinity matrix or solid support. The BABS-streptavidin protein could then be bound to the matrix or support for affinity chromatography or solid phase immunoassay. The interleukin-2 construct could be linked, for example, to a BABS specific for a T-cell surface antigen. The FB-FB dimer binds to Fc, and could be used with a BABS in an immunoassay or affinity purification procedure linked to a solid phase through immobilized immunoglobulin.

FIG. 14 exemplifies a multifunctional protein having an effector segment as a leader. It comprises an FB-FB dimer linked through its C-terminal via an Asp-Pro dipeptide to a BABS of choice. It functions in a way very similar to the construct of FIG. 15H. The dimer binds avidly to the Fc portion of immunoglobulin. This type of construct can accordingly also be used in affinity chromatography, solid phase immunoassay, and in therapeutic contexts where coupling of immunoglobulins to another epitope is desired.

In view of the foregoing, it should be apparent that the invention is unlimited with respect to the specific types of BABS and effector proteins to be linked. Accordingly, other embodiments are within the following claims.

What is claimed is:

1. A host cell harboring and capable of expressing a DNA encoding a biosynthetic single chain polypeptide, said single chain polypeptide comprising:

a linking sequence connecting first and second non-naturally peptide-bonded, biologically active polypeptide domains to form a single polypeptide chain comprising at least two biologically active domains, connected by said linking sequence, said linking sequence comprising hydrophilic, peptide-bonded amino acids comprising at least 10 amino acid residues, said linking sequence being cysteine-free, having a flexible unstructured polypeptide configuration essentially free of secondary structure in aqueous solution, having a plurality of glycine or serine residues and defining a polypeptide of a length sufficient to span the distance between the C-terminal end of the first domain and the N-terminal end of the second domain.

2. The host cell of claim 1, wherein said host cell is a prokaryotic cell.

3. The host cell of claim 2, wherein said prokaryotic cell is *E. coli.*

4. The host cell of claim 1, wherein said host cell is a eukaryotic cell.

5. The host cell of claim 3, wherein said eukaryotic host cell is a Chinese hamster ovary cell, murine myeloma cell, human myeloma cell or a human transfectoma cell.

6. A method of producing a biosynthetic single chain polypeptide, said method comprising the steps of:

(a) providing a prokaryotic host cell that expresses a DNA encoding a biosynthetic single chain polypeptide, said single chain polypeptide comprising a linking sequence connecting first and second non-naturally peptide-bonded, biologically active polypeptide domains to form a single polypeptide chain comprising at least two biologically active domains, connected by said linking sequence, said linking sequence comprising hydrophilic, peptide-bonded amino acids comprising at least 10 amino acid residues, said linking sequence being cysteine-free, having a flexible unstructured polypeptide configuration essentially free of secondary structure in aqueous solution, having a plurality of glycine or serine residues and defining a polypeptide of a length sufficient to span the distance between the C-terminal end of the first domain and the N-terminal end of the second domain;

(b) culturing said host cell under conditions to promote expression of said polypeptide in said host cell; and (c) harvesting said polypeptide.

7. A method of producing a biosynthetic single chain polypeptide, said method comprising the steps of:

providing a eukaryotic host cell that expresses a DNA encoding a biosynthetic single chain polypeptide, said single chain polypeptide comprising a linking sequence connecting first and second non-naturally peptide-bonded, biologically active polypeptide domains to form a single polypeptide chain comprising at least two biologically active domains, connected by said linking sequence, said linking sequence comprising hydrophilic, peptide-bonded amino acids comprising at least 10 amino acid residues, said linking sequence being cysteine-free, having a flexible unstructured polypeptide configuration essentially free of secondary structure in aqueous solution, having a plurality of glycine or serine residues and defining a polypeptide of a length sufficient to span the distance between the C-terminal end of the first domain and the N-terminal end of the second domain;

(b) culturing said host cell in a medium under conditions to promote expression and secretion of said polypeptide into the medium; and (c) harvesting said polypeptide from the medium.

* * * * *

UNITED STATES PATENT AND TRADEMARK OFFICE
CERTIFICATE OF CORRECTION

PATENT NO. : 5,482,858
DATED : January 9, 1996
INVENTOR(S) : James S. Huston and Hermann Oppermann It is certified that error appears in the above-indentified patent and that said Letters Patent is hereby corrected as shown below:

Col. 28, claim 5, line 63, change "3" to -- 4 --.

Col. 30, claim 7, line 1, before "providing" insert -- (a) --.

Signed and Sealed this

Twenty-sixth Day of November 1996

Attest:

BRUCE LEHMAN

Attesting Officer

Commissioner of Patents and Trademarks